United States Patent
Kelley et al.

(10) Patent No.: US 9,358,138 B2
(45) Date of Patent: Jun. 7, 2016

(54) POLYMERIC PROSTHETIC DEVICES WITH HEAT CONTROL CAPABILITIES

(71) Applicant: The Ohio Willow Wood Company, Mount Sterling, OH (US)

(72) Inventors: Christopher T. Kelley, Grandview Heights, OH (US); Michael L. Haynes, Columbus, OH (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 0 days.

(21) Appl. No.: 14/133,485

(22) Filed: Dec. 18, 2013

(65) Prior Publication Data

US 2014/0309750 A1    Oct. 16, 2014

Related U.S. Application Data

(63) Continuation-in-part of application No. 13/949,218, filed on Jul. 23, 2013.

(60) Provisional application No. 61/674,597, filed on Jul. 23, 2012.

(51) Int. Cl.
*A61F 2/80* (2006.01)
*A61F 2/78* (2006.01)
*A61F 7/02* (2006.01)
*A61F 5/01* (2006.01)
(Continued)

(52) U.S. Cl.
CPC .................. *A61F 2/80* (2013.01); *A61F 2/7812* (2013.01); *A61F 5/01* (2013.01); *A61F 7/02* (2013.01); *A61F 2002/501* (2013.01); *A61F 2002/5012* (2013.01); *A61F 2002/5055* (2013.01); *A61F 2007/0051* (2013.01); *A61F 2007/0225* (2013.01); *A61F 2007/0246* (2013.01); *A61F 2007/0247* (2013.01); *A61F 2007/0292* (2013.01); *Y10T 29/49826* (2015.01)

(58) Field of Classification Search
CPC ........... A61F 2/78; A61F 2/7812; A61F 2/80; A61F 2/7843; A61F 2002/501–2002/5013; A61F 2007/0051
See application file for complete search history.

(56) References Cited

U.S. PATENT DOCUMENTS

| | | | |
|---|---|---|---|
| 4,964,402 A | 10/1990 | Grim et al. | |
| 5,722,482 A | 3/1998 | Buckley | |
| 6,010,528 A * | 1/2000 | Augustine | A61F 2/7843 297/452.21 |

(Continued)

FOREIGN PATENT DOCUMENTS

DE    102010020262 A1 * 11/2011

OTHER PUBLICATIONS

International Search Report and Written Opinion for related PCT Application No. PCT/US2013/051748 mailed on Nov. 8, 2013.
(Continued)

*Primary Examiner* — Marcia Watkins
(74) *Attorney, Agent, or Firm* — Benesch Friedlander Coplan & Aronoff LLP; Benjamen E. Kern; Steve D. Scanlon

(57) ABSTRACT

Prosthetic liners, prosthetic sockets and prosthetic suspension sleeves, as well as orthotic components, having enhanced thermally conductivity and/or enhanced heat absorption capabilities. Such components may be used in various combinations to create assemblies and systems that are operative to better transfer heat away from and/or absorb heat produced by residual or intact limbs of a user.

15 Claims, 26 Drawing Sheets

(51) Int. Cl.
 *A61F 2/50* (2006.01)
 *A61F 7/00* (2006.01)

(56) References Cited

U.S. PATENT DOCUMENTS

| | | |
|---|---|---|
| 6,123,716 A | 9/2000 | Augustine et al. |
| 6,547,824 B1 | 4/2003 | Price |
| 2002/0103539 A1 | 8/2002 | Stelter |
| 2002/0103545 A1 | 8/2002 | Arbogast et al. |
| 2002/0173856 A1* | 11/2002 | Karason .................... 623/37 |
| 2005/0101693 A1 | 5/2005 | Arbogast et al. |
| 2005/0240283 A1 | 10/2005 | Kania |
| 2006/0213173 A1 | 9/2006 | Kolmes et al. |
| 2007/0135878 A1* | 6/2007 | Lachenbruch ............ A61F 7/10 607/108 |
| 2009/0240344 A1 | 9/2009 | Colvin et al. |
| 2010/0274364 A1 | 10/2010 | Pacanowsky et al. |
| 2011/0193008 A1 | 8/2011 | Fieback et al. |
| 2011/0220841 A1* | 9/2011 | Zheng et al. .................... 252/71 |
| 2013/0274896 A1 | 10/2013 | Wang et al. |
| 2014/0005800 A1 | 1/2014 | Kelley et al. |
| 2014/0058529 A1 | 2/2014 | Schober et al. |
| 2014/0277585 A1 | 9/2014 | Kelley et al. |

OTHER PUBLICATIONS

Extended European Search Report in related European Patent Application No. 13822435.7, Jan. 11, 2016.

* cited by examiner

SECTION A-A

SECTION A-A

SECTION A-A

SECTION A-A

SECTION A-A

SECTION A-A

SECTION A-A

SECTION A-A

SECTION B-B

SECTION B-B

SECTION C-C

SECTION C-C

POLYMERIC PROSTHETIC DEVICES WITH HEAT CONTROL CAPABILITIES

CROSS-REFERENCE TO RELATED APPLICATIONS

The present application is a continuation-in-part of U.S. patent application Ser. No. 13/949,218 filed on Jul. 23, 2013, which claims the benefit of U.S. Provisional Application No. 61/674,597 filed on Jul. 23, 2012.

TECHNICAL FIELD

The invention is directed to prosthetic and orthotic devices with optimized heat transfer and/or heat absorption capabilities, including but not limited to, polymeric prosthetic liners, prosthetic sockets, prosthetic assemblies including such liners and sockets, and orthotic braces, boots and insoles.

BACKGROUND

Polymeric prosthetic liners (hereinafter also referred to as "prosthetic liners" or "liners") have become the interface of choice among amputees due to various beneficial characteristics thereof. These characteristics include, for example, comfort, security of suspension, protection of the residual limb, and ease of use. Modern liner technology allows amputees to employ a liner as the sole (stand-alone) interface between their residual limb (which is also commonly referred to as a residuum or amputation stump) and the interior of a prosthetic socket.

Polymeric prosthetic liners generally come in two primary forms—with a distal connecting element or without a distal connecting element. Prosthetic liners that lack a connecting element are commonly referred to as "cushion liners," although such liners can still serve a suspensory function. Prosthetic liners that include a connecting element, which acts to facilitate suspension by mechanical attachment of the liner to a prosthesis, are commonly referred to as "locking liners." Prosthetic liners can be of standard "off-the-shelf" design, meaning the liner is of generic shape and will fit a range of residual limb shapes and sizes. Alternatively, liners may be custom designed for a particular amputee.

Liners may be comprised of various polymeric materials; including silicone, urethane, and thermoplastic elastomer (TPE) gels. Liners are now commonly made using various block copolymer and mineral oil gel compositions, as well as silicone and blended silicone compositions. Such polymeric materials have proven themselves to provide a high level of comfort for most users.

It is also known to construct such liners with an outer layer of fabric. That is, there exist patented fabric-covered liners having an interior of exposed polymeric gel for contacting and cushioning an amputee's residual limb, and an outer layer of fabric for, among other things, increasing the wear resistance of the liner, and facilitating donning/doffing and insertion of the liner-covered residual limb into a prosthetic socket. Such patented fabric-covered liner products are available from The Ohio Willow Wood Company in Mt. Sterling, Ohio.

Liners as described above may be used by upper limb amputees but are probably more frequently used by lower limb amputees. Lower limb amputees generally fall into one of two categories: below knee (BK) amputees and above knee (AK) amputees. In the case of a BK amputee, the amputation may occur through the tibia (i.e., is trans-tibial) or through the ankle (i.e., a Syme's amputation) and the knee joint is still present on the residual limb. Thus, a bending of the residual limb at the knee joint will still occur during ambulation. In the case of an AK amputee, the amputation may occur through the femur (i.e., is trans-femoral) or knee (i.e., a knee disarticulation) and the knee joint is missing from the residual limb.

In any case, and as would be well understood by one of skill in the art, an amputee typically dons a prosthetic liner, such as by rolling it onto the residual limb, and then inserts the liner-covered residual limb into a socket portion of a prosthesis. The prosthesis may be suspended (secured) on the liner-covered limb by means of, for example, vacuum, by a mechanical attachment such as a pin and lock mechanism, by friction alone, by use of a suspension sleeve, or by a combination thereof.

As would also be understood by one of skill in the art, a residual limb can become quite warm when covered with a polymeric prosthetic such as those described above, due largely to the substantially non-breathable and minimally thermally conductive nature of the silicone, urethane, TPE and other polymeric materials that are generally used. This heat retention problem may be further compounded when the exterior of the polymeric material is covered with a fabric, as described above. As it is desirable to employ a fabric that is durable and will prevent the bleed-through of polymeric material to the exterior of the fabric, the fabric may itself serve as another cause of heat retention.

The prosthetic socket into which a liner-covered residual limb is inserted may also contribute to the aforementioned heat retention problem. Since prosthetic sockets are commonly formed from fiberglass, composites, thermoplastics, resins, and other rigid and impermeable or substantially impermeable materials with comparably low thermal conductivities, heat transfer through the prosthetic socket is typically inhibited if not prevented.

As can be understood then, when a polymeric liner-covered residual limb is inserted into a prosthetic socket, both the liner and the prosthetic socket may cause the residual limb to retain heat. This effect may be exacerbated when the prosthetic liner also includes a fabric-covered exterior. If a suspension sleeve is used, it too can contribute to the heat retention problem, since such sleeves are also typically of a polymer and fabric construction. The results of this heat retention may include, for example, an uncomfortable warming of the residual limb and/or excessive perspiration that can lead to skin problems. In fact, at least one study has shown that heat/sweating in the prosthetic socket is considered by many amputees to be the predominant problem associated with the wearing of a prosthesis. (See e.g., *Consequences of non-vascular trans-femoral amputation: a survey of quality of life, prosthetic use and problems*, K. Hagberg and R. Branemark, Prosthetics and Orthotics International, 2001, 25, 186-194).

In recognition of this residual limb heating problem, commercially available prosthetic liners and sockets have been analyzed with respect to their thermal conductivity properties and it has been shown that both prosthetic liners and prosthetic sockets contribute to residual limb heating. One such study reveals that a sample of several commercially available prosthetic liners exhibits a thermal conductivity of between 0.085-0.266 W/(m·° K), while a sample of several commercially available prosthetic socket materials exhibits a thermal conductivity of between 0.148-0.150 W/(m·° K). (See *The thermal conductivity of prosthetic sockets and liners*, G. K. Klute, G. I. Rowe, A. V. Mamishev, & W. R. Ledoux, Prosthetics and Orthotics International, September 2007, 31(3), 292-299.)

Similarly, orthotic devices can also suffer from heat retention problems. For example, knee sleeves and braces, ankle-foot orthoses (AFOs), knee-ankle-foot orthoses (KAFOs), walker boots, shoe insoles, back braces, and other braces can include polymers for padding, fabrics, resins, and reinforcements as used in prosthetic liners and sockets.

Importantly, patient testing has revealed that humans are capable of detecting the results of even small improvements in thermal conductivity when it comes to a device such as a prosthetic liner. For example, test patients unsolicitedly reported a perceived reduction in residual limb temperature (i.e., their residual limbs felt cooler) when wearing prosthetic liners whose polymeric material was silicone instead of a block copolymer and mineral oil gel composition. This is despite the fact that the difference in thermal conductivity between the particular silicone material and block copolymer and mineral oil gel composition in question was only about 0.04 W/(m·° K). Consequently, enhancing the thermal conductivity of prosthetic and/or orthotic devices to an even more substantial degree may bring about even greater patient comfort through further reduced limb temperatures.

It can be understood from the foregoing discussion that there is a need for various prosthetic and orthotic devices that maximize heat transfer from the associated residual limb or intact limb of the user and/or provide for the enhanced absorption of residual limb heat—the meaning of which is explained in more detail below. Exemplary prosthetic devices and assemblies according to the invention may include, without limitation, a polymeric prosthetic liner, a prosthetic suspension sleeve, a prosthetic socket, and a prosthetic assembly that includes such a prosthetic liner along with a prosthetic socket and, optionally, a prosthetic suspension sleeve. Such orthotic devices may include, without limitation, an AFO, a KAFO, a knee sleeve, a walker boot, a shoe insole, a back brace, and other braces, as mentioned above, as well as any other orthotic device that includes similar materials of construction.

SUMMARY

Prosthetic liner embodiments of the invention are designed to enclose at least a portion of a residual limb. As such, a liner embodiment according to the invention will generally include an open end for allowing introduction of the residual limb, and a closed end opposite the open end. The closed end generally abuts and cushions the distal end of the residual limb when the liner is worn. Such a liner may be used by an upper or lower extremity amputee.

Prosthetic socket embodiments of the invention are designed to receive, retain and support a residual limb, such as a liner-covered residual limb. Prosthetic socket embodiments of the invention are also designed to couple the residual limb to the remainder of an associated prosthesis. Therefore, when a prosthetic socket is a part of a BK prosthesis, a pylon or similar element may be attached to the distal end of the socket for coupling the socket to a prosthetic ankle or foot. When a prosthetic socket is a part of an AK prosthesis, similar prosthetic components may be coupled thereto, but with a prosthetic knee joint residing between the other components and the socket.

Suspension sleeve embodiments of the invention are typically worn in conjunction with a prosthetic socket. That is, once an amputee has inserted his/her residual limb into the socket of a prosthesis, a suspension sleeve may be donned to seal the open (proximal) end of the socket. When used in this manner, one end of the suspension sleeve is located to overlie the proximal end of the socket while the other end of the suspension sleeve is located to overlie a portion of the amputee's residual limb (which may be covered by a prosthetic liner). In this manner, air may be prevented from entering or exiting the socket from the proximal end thereof, thereby facilitating creation and maintenance of a vacuum within the socket. The ability to create and maintain vacuum within a socket can be particularly valuable when the associated prosthesis is retained on the residual limb by means of active vacuum or suction suspension. Such a suspension sleeve may be used by an upper or lower extremity amputee.

Liner embodiments of the invention are generally comprised of a polymeric material, the exterior of which may be covered partially or entirely with fabric. A fabric-covered liner embodiment of the invention thus includes a polymeric material interior and a partial or wholly fabric exterior. When used with a prosthesis, the polymeric material of the liner interior is in contact with the skin of a residual limb and the fabric exterior is in contact with the interior of a prosthetic socket. Alternatively, liner embodiments according to the invention may be entirely devoid of fabric. When fabric is absent or partially absent from the exterior of a liner, the exposed polymeric material may be covered by/coated with a layer of lubricious material, such as but not limited to parylene.

Suspension sleeve embodiments of the invention are also generally comprised of a polymeric material, the exterior of which may again be covered partially or entirely with fabric. A fabric-covered suspension sleeve embodiment of the invention thus may include a polymeric material interior and a partial or wholly fabric exterior. As with liner embodiments of the invention, other suspension sleeve embodiments may also be wholly devoid of exterior fabric and a layer of a lubricious material such as parylene may optionally cover or be coated on any exposed exterior polymeric material. Suspension sleeve embodiments of the invention may also include an interior band of fabric. When used with a prosthesis, the polymeric material interior at one end of the suspension sleeve is in contact with the skin of a residual limb or an exposed area of liner polymer, while the polymeric material interior at the other end of the suspension sleeve is in contact with an exterior surface of a prosthetic socket.

Orthoses are externally applied devices used to support the musculoskeletal system. Orthoses are commonly used to control motion of a joint, to reduce weight-bearing forces, or otherwise support or shape the body. Some commonly used orthoses include upper limb-limb orthoses, foot orthoses, ankle-foot orthoses (AFOs), knee-ankle-foot orthoses (KAFOs), knee orthoses, and spinal orthoses.

Foot orthoses are inserts for a shoe used to distribute pressure or realign the foot. An AFO is a brace to support the ankle and foot, and is used to properly position a deformed limb or to provide support for a weak limb. A KAFO is a brace to support the knee, ankle, and foot that is used to properly position a deformed limb or to provide support for a weak limb. A knee orthosis is a brace to support the knee that is used to properly position a deformed knee or to provide support for a knee. A spinal orthosis is a brace which can be used to treat abnormal curvature of the spine or to restrict motion of the spine.

Orthoses are made from materials that are commonly the same as or similar to those used in making prostheses, including fiber reinforcement, composites, thermoplastic, resin and other rigid and semi-rigid materials. Polymeric materials or other elastomers and fabrics can also be used to improve the comfort of orthoses. Since the orthoses are in intimate contact with the body and many of such materials are substantially impermeable, heat transfer through the orthoses is typically inhibited if not prevented, just as with prostheses. Therefore, current orthoses can be uncomfortable and can be improved by using the thermally enhanced materials described in this application for the use in prostheses.

The polymeric material portion of a liner, suspension sleeve, or orthotic device embodiment of the invention may be comprised of, without limitation, silicone (including thermoplastic silicone, thermoset silicone and silicone gels), urethane (including thermoset urethane and thermoplastic urethane), a silicone polyurethane copolymer, a thermoplastic elastomer (TPE), or a combination thereof. Of particular interest are block copolymer gel compositions, and silicone compositions, as such materials have proven to be especially effective at cushioning and protecting residual limbs while simultaneously providing amputees with a high level of comfort.

Because the polymeric material of the liner interior will normally be in contact with the skin of a residual limb when the liner is worn, the polymeric material is generally smooth and continuous in nature such that there are preferably no seams or other discontinuities that may cause amputee discomfort. A liner of the present invention will typically protect and cushion the entire portion of a residual limb residing in a prosthetic socket.

While a liner of the present invention may be of a non-locking (i.e., cushion) variety, other embodiments are constructed as locking liners. To this end, a liner of the present invention may include a connecting element at the closed end for facilitating attachment of the liner to the prosthetic socket of a prosthetic limb. Such connecting elements may be designed with a base portion that has a special accordion shape, which provides for increased comfort when the liner is worn by better conforming to the distal shape of the residual limb.

Liners of the invention are preferably constructed with polymeric materials that are modified to optimize the transfer of heat away from the residual limb (i.e., to exhibit maximum thermal conductivity) and to the exterior of the liner, and/or to provide for the enhanced absorption of heat emitted by the residual limb. It is realized that many materials can transfer or absorb heat to some degree. Therefore, it is to be understood that the concept of enhanced "heat transfer" and/or "thermal conductivity", as used herein, refers to the ability of exemplary prosthetic or orthotic device embodiments to transfer heat away from a residual or intact limb at a rate and/or with an efficiency that is superior to the rate and/or efficiency at which such heat transfer would occur in polymeric prosthetic liners and suspension sleeves of typical (i.e., non-enhanced) design and construction. In other words, prosthetic and orthotic device embodiments of the invention may have heat transfer capabilities that are optimized, maximized, improved, etc., in comparison to typically constructed prosthetic and orthotic devices. Similarly, as used herein, the concept of enhanced heat "absorption" refers to the ability of an exemplary prosthetic or orthotic device to absorb heat from a residual limb or intact limb, within some temperature range, without any significant increase in localized temperature. In other words, exemplary prosthetic and/or orthotic device embodiments of the invention may include a material(s) that has a latent heat capacity sufficient to absorb a given amount of heat from a residual or intact limb with no or only a minimal increase in the temperature of the liner or suspension sleeve.

In this regard, the polymeric material of a given liner, suspension sleeve, or orthotic device may be doped with or otherwise include additives/fillers that improve the heat transfer capabilities of the base polymeric material. A number of potentially usable thermally conductive additives/fillers are described in more detail below.

In addition, it is possible to employ one or more encapsulated and/or un-encapsulated phase change materials as a heat absorbing additive. In this regard, exemplary embodiments of a prosthetic or orthotic device of the invention may include materials that are doped with or otherwise include one or more encapsulated and/or un-encapsulated phase change materials, such as a phase change material(s) that is dispersed within the polymeric material of the devices as a heat absorbing additive. Alternatively, a phase change material layer of some thickness may be provided, preferably along an area of a liner, prosthetic socket, suspension sleeve or orthotic device that will reside against or near the skin of a residual or intact limb when worn. In either case, the use of a phase change material(s) can act as a buffer against an increase (or decrease) in temperature inside a liner and socket assembly. Consequently, phase change materials may act to reduce peak heat loads in a prosthetic system by absorbing heat for later release and, therefore, may also reduce the amount of thermal conductivity required by a liner and socket system in order to keep a residual limb adequately cool. The use of phase change materials may thus also allow the consideration of a larger range of thermally conductive additives/fillers (i.e., additives/fillers that exhibit a lesser thermal conductivity) for use in the liner and socket assembly.

In other embodiments, liners, suspension sleeves and orthotic devices of the invention may include fluid-filled pockets that help to conduct heat away from the residual limb. Such fluid-filled pockets may operate to both increase the thermal conductivity of a given device, and to facilitate the transfer of heat by convection and other currents induced by the motion of the liner, socket, and/or suspension sleeve.

In yet other embodiments, liners, suspension sleeves and orthotic devices of the invention may include one or more areas of high thermal conductivity within the polymeric material. These area(s) of high thermal conductivity may be comprised of, for example, one or more polymeric materials that are dissimilar to the polymeric material forming the primary portion of the liner, suspension sleeve or orthotic device, and which exhibit better thermal conductivity.

In yet other liners, suspension sleeve and orthotic device embodiments, a bladder(s) or similar container(s) of an encapsulated or un-encapsulated phase change material, such as a wax-type, phase change material, may be employed. The bladder(s) may be molded with and may become integral to the liner, suspension sleeve or orthotic device. When the liner, suspension sleeve or orthotic device is worn, the phase change material absorbs heat generated by the residual or intact limb over which the liner, suspension sleeve or orthotic device is donned, and the heat is released after doffing thereof.

Additional liner embodiments having enhanced heat absorption capabilities may include a phase change material with a phase transition temperature that is lower than the typical temperatures experienced within a prosthetic liner during use by an amputee, such that the phase change material will always reside in a liquid state when the liner is in use. In the case of a liner whose polymeric material is silicone, for example, the use of such a phase change material allows the silicone to exhibit the desired enhanced heat absorption capabilities, while also simultaneously having a lower hardness value (i.e., a softer liner) but with a creep value that is similar to that of a harder silicone.

Liners, suspension sleeves and orthotic devices of the invention having a fabric covered exterior may also be constructed with fabric materials that exhibit good thermal conductivity, or are modified to enhance thermal conductivity, so as to better transfer heat away from the associated limb after conductive transfer by the polymeric material. Such fabric materials and modifications to fabric materials are described in more detail below and may include the use of, without limitation, conductive coatings, multi-component yarns, conductive filler doping, phase change materials, knit-in or wound wires, and regions that permit the penetration therethrough of the polymeric material.

As with liners of the invention, it is also preferred that prosthetic sockets used with the invention be comprised of a material that exhibits good thermal conductivity so as to effectuate the transfer of heat away from the residual limb residing therein. In this regard, the material used to construct a given prosthetic socket may include additives/fillers that improve the heat transfer characteristics of the socket material and/or buffer temperature. A number of potentially usable additives/fillers are described in more detail below. These additives/fillers may again include phase change materials.

It is also possible to construct a prosthetic socket of the invention entirely from a conductive material using an additive manufacturing technique such as, for example, selective laser sintering (SLS). It is further possible to employ passive heat transfer devices that may be coupled to a prosthetic socket. Such devices may include, for example, heat pipes, vapor chambers, aluminum or other thermally conductive metal elements, and heat sinks. Active cooling mechanisms, such as Peltier devices, and cooling channels or cooling tubes through which is circulated a cooling fluid, may also be associated with the socket.

Prosthetic sockets may also employ phase change materials in lieu of or in addition to thermal conductivity enhancing additives/fillers. A phase change material may be dispersed within the base material of a prosthetic socket and/or provided in one or more layers therein. In another exemplary embodiment, a prosthetic socket of the invention may employ a phase change material having a melting point well below the temperature at which an amputee would start to perceive discomfort from excessively high temperatures, so as to facilitate high heat flows. A heat switch may be provided to actively or passively regulate the heat flow of a prosthetic socket embodiment utilizing a phase change material having such a low melting point. A better understanding of various prosthetic and orthotic device embodiments according to the invention can be gained by review of the following description of several exemplary embodiments thereof, along with the associated accompanying drawing figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF THE EXEMPLARY EMBODIMENT(S)

Figure 1A:
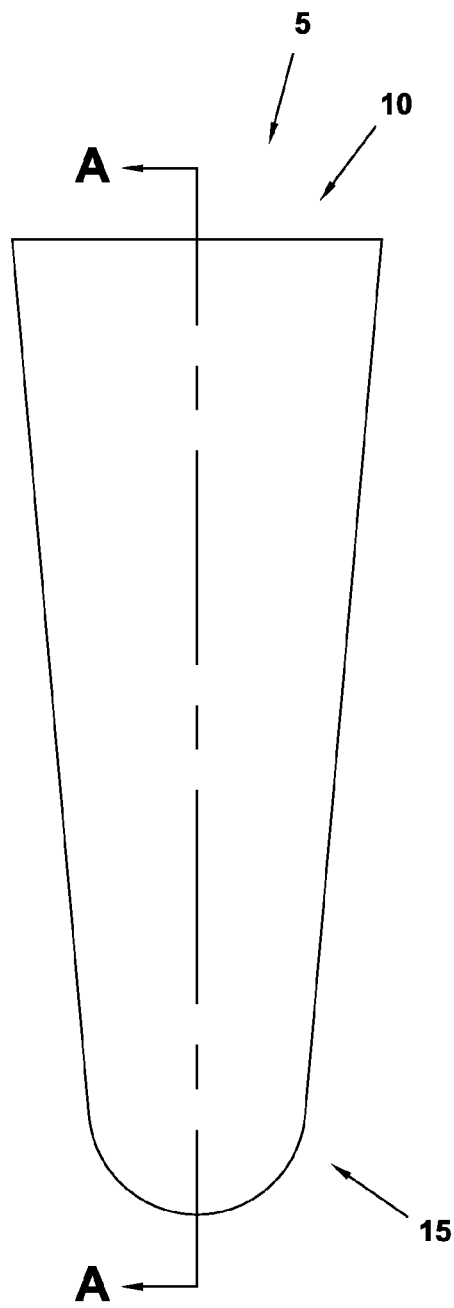
FIG. 1A represents an exemplary embodiment of a non-locking prosthetic liner of the invention.

Prosthetic liner embodiments of the invention may be wholly fabric covered, partially fabric covered, or completely lacking a fabric covering. In the latter case, a lubricious coating (e.g., parylene) may or may not be provided on the polymeric liner exterior. Prosthetic liner embodiments of the invention may be non-locking in nature, i.e., without a distal connecting element. Prosthetic liners of the invention may also be locking in nature, i.e., with a distal connecting element. Liners of the invention may be of "off-the-shelf" design or may be custom designed for a particular amputee. Liners of the invention may be designed for use by upper limb amputees, or by either AK or BK lower limb amputees. Liners of the invention may function as a standalone interface between an amputee's residual limb and the interior of a prosthetic socket in use or, optionally, may be used in conjunction with a sheath, sleeve, or additional limb-covering element.

Locking liner embodiments of the invention may be provided with a distal connector assembly, such as, but not limited to, the connecting element shown and described in U.S. patent application Ser. No. 12/711,234, which was filed on Feb. 23, 2010 and is incorporated by reference herein. While not limited thereto, the polymeric material of a liner of the invention may be provided in any of the profiles shown and described in U.S. patent application Ser. No. 12/711,234, such as for example, the profiles depicted in FIGS. 3, 4, 6, and 9a-9b. When a liner of the invention is provided with a partially or wholly fabric-covered exterior, the fabric(s) used, as well as the shape, location, arrangement, etc., of the fabric(s) may also be as shown and described in U.S. patent application Ser. No. 12/711,234, such that the longitudinal stretch (elasticity) of a liner of the invention may be controlled primarily by its fabric exterior. Non-stretch controlling fabrics and fabric arrangements may also be employed.

Prosthetic suspension sleeve embodiments of the invention may be provided with a partially or wholly fabric-covered exterior. Prosthetic suspension sleeve embodiments of the invention may also have an exterior comprised of exposed polymeric material (i.e., no fabric covering). In such a latter embodiment, a lubricious coating may or may not be provided on the suspension sleeve exterior. Prosthetic suspension sleeve embodiments of the invention may be provided with an interior fabric band(s) at particular locations.

While not limited to such a construction, prosthetic suspension sleeve embodiments of the invention may be designed and constructed as shown and described in U.S. Pat. No. 6,406,499, and/or as shown and described in U.S. patent application Ser. No. 11/855,866, which was filed on Sep. 14, 2007.

Exemplary embodiments of a prosthetic liner with enhanced thermal conductivity and/or enhanced heat absorption capabilities are described below, as are exemplary embodiments of a prosthetic suspension sleeve with enhanced thermal conductivity and/or enhanced heat absorption capabilities, and exemplary embodiments of a prosthetic socket with enhanced thermal conductivity. These exemplary embodiments are provided solely for the purpose of illustration, and not limitation. As described above, each exemplary embodiment of a liner and suspension sleeve includes a polymeric material, the exterior of which may be partially or completely covered with fabric, or wholly devoid of fabric.

With respect to the cross-sectional views illustrated herein, it should be noted that the drawing figures are not necessarily drawn to scale. For example, the thickness of the fabric layers and the polymeric material layers of the exemplary liners and suspension sleeves may be exaggerated for clarity. Further, the fabric layers and polymeric material layers are not necessarily drawn to scale with respect to each other. The same may hold true for the exemplary prosthetic socket embodiments shown in the accompanying drawing figures, as well as for the assemblies of various ones of said components.

Figure 1B:
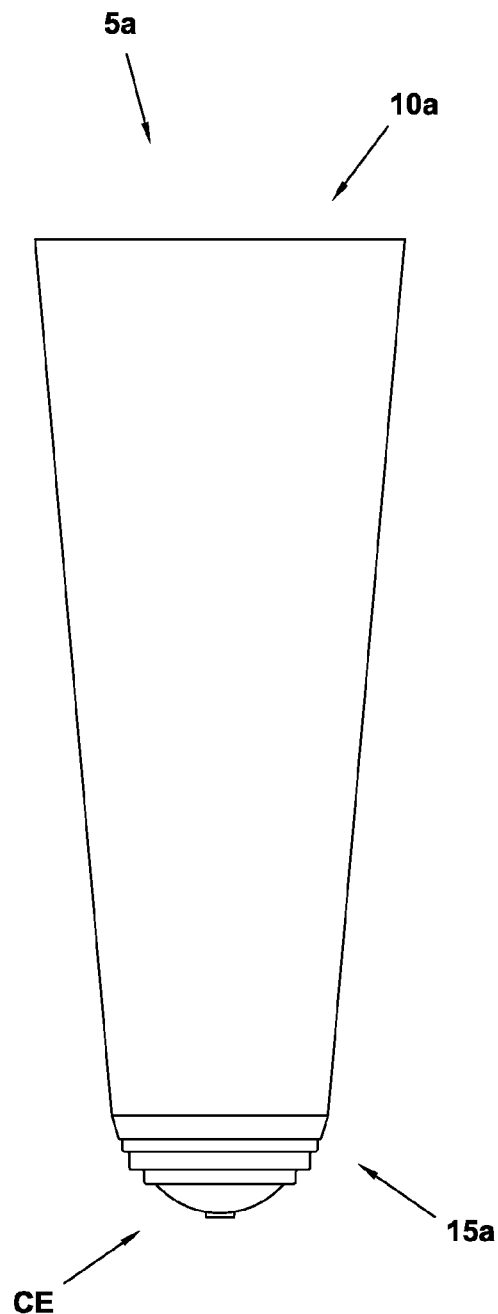
FIG. 1B represents an exemplary embodiment of a locking prosthetic liner of the invention.

A first embodiment of a non-locking prosthetic liner 5 of the invention having enhanced thermal conductivity (heat transfer capabilities) is depicted in FIG. 1A. As shown, the liner 5 includes an open end 10 for permitting insertion of a residual limb, and a closed end 15 opposite the open end. A locking version of the prosthetic liner 5 of FIG. 1A is illustrated in FIG. 1B. The locking liner 5b has substantially the same construction as the non-locking liner 5 and, therefore, also includes an open end 10a for permitting insertion of a residual limb, and a closed end 15a opposite the open end. Unlike the non-locking liner 5, the locking liner 5a further includes a distal connecting element CE for mechanically coupling the liner to a prosthetic socket. The connecting element CE may include a threaded female bore (or insert) that is adapted to receive a like-threaded male pin (not shown), as would be familiar to one of skill in the art.

Figure 2:
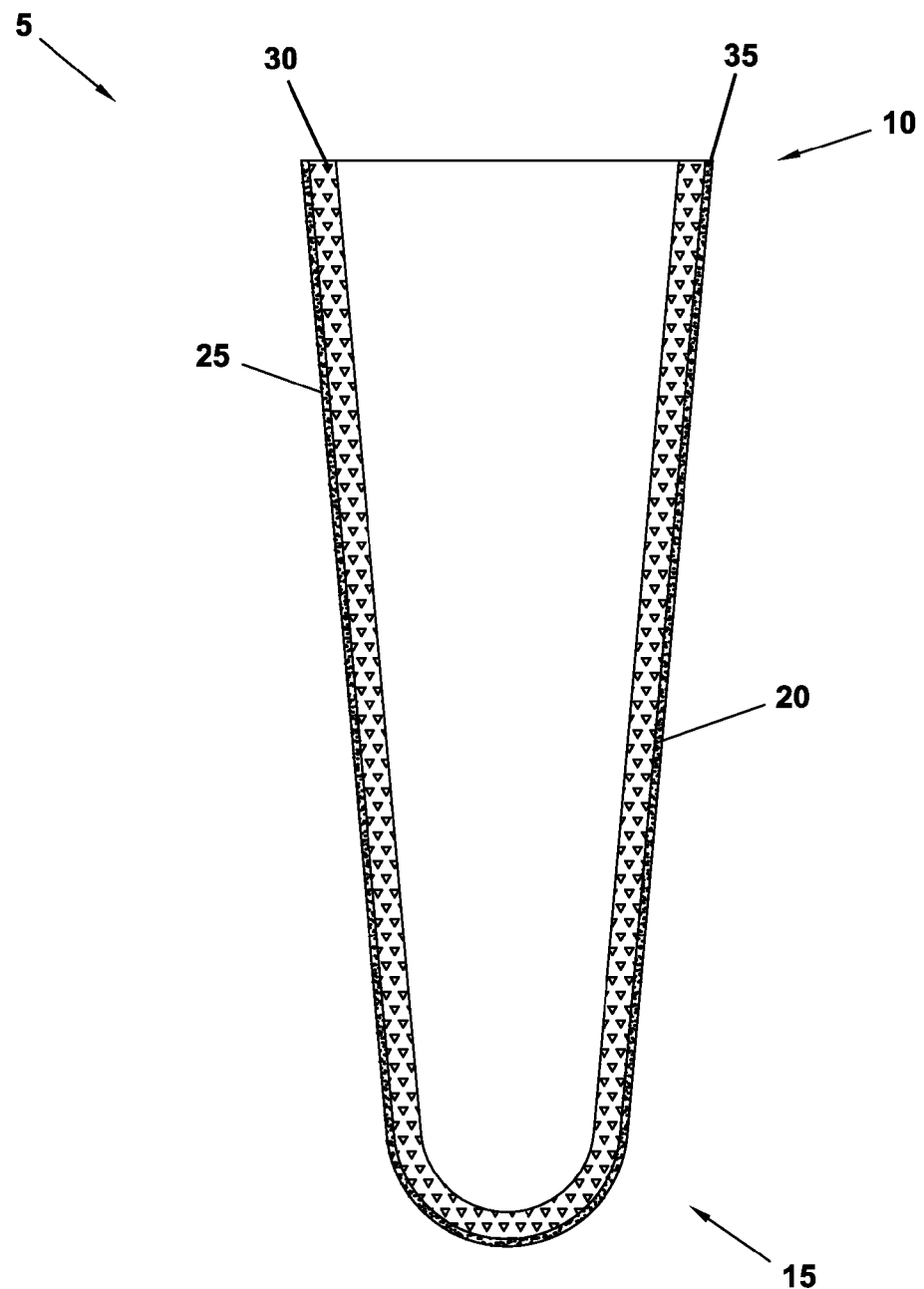
FIG. 2 is a cross-sectional view of an exemplary embodiment of a prosthetic liner of the invention.

A cross-sectional view of the liner 5 of FIG. 1A can be observed in FIG. 2. As shown, the interior of the liner 5 is comprised of a polymeric material 20 while the exterior of the liner is comprised of fabric 25. The polymeric material 20 of the liner interior is arranged so as to typically be in contact with the skin of a residual limb when the liner is worn. The fabric portion 25 is arranged so as to typically be in contact with the interior of a prosthetic socket when the liner is used with a prosthetic limb, although this may not be the case in all embodiments.

The polymeric material portion of a liner of the invention may be comprised of, without limitation, silicone (including thermoplastic silicone, thermoset silicone and silicone gels), urethane (including thermoset urethane and thermoplastic urethane), a silicone polyurethane copolymer, or a thermoplastic elastomer (TPE) such as a block copolymer and mineral oil gel composition. Certain embodiments may employ a combination of such materials. For example, the polymeric material may comprise a TPE inner layer for contact with a residual limb, and a harder outer layer, such as a layer constructed of silicone or urethane. Such an embodiment is taught in U.S. patent application Ser. No. 12/407,362 filed on Mar. 19, 2009.

The liner 5 of FIG. 2 represents an exemplary embodiment where the heat transfer capability of the polymeric material 20 has been enhanced by the inclusion therein of additives/fillers 30. In this exemplary embodiment, the additives/fillers 30 are dispersed within the polymeric material.

Suitable additives/fillers for increasing the thermal conductivity of polymeric materials (such as those listed above) used in prosthetic liners, prosthetic suspension sleeves and orthotic devices according to the invention may include, without limitation, fullerenes such as carbon nanotubes; graphene platelets; boron nitride platelets; boron nitride fibers; boron nitride spherical powder; boron nitride agglomerates; diamond powder; graphite fibers; powders of silver, copper, gold and aluminum oxide; aluminum powder; and various combinations of two or more such additives/fillers. The use of one or more of these materials may enhance the heat transfer capability of a base polymeric material or polymeric material composition. For example, it has been found through experimentation that the addition of graphene platelets to a block copolymer and mineral oil gel composition can raise the thermal conductivity thereof from about 0.2 to above 0.4 W/(m·° K). Prosthetic liners according to the invention are expected to exhibit enhanced thermal conductivity of at least about 0.3 W/(m·° K).

As described above, the fabric used in a liner of the invention may inherently exhibit good thermal conductivity. Alternatively, and as represented in FIG. 2, the fabric 25 of the liner 5 may be modified to produce or enhance the thermal conductivity thereof. As such modifications would typically be invisible to the naked eye, various possible thermal conductivity enhancements of the fabric 25 are generally represented in FIG. 2 by reference number 35.

Thermal conductivity enhancements of the fabric 25 may include, without limitation, the use of multi-component yarns. Such yarns would be generally familiar to one of skill in the art and may also be referred to as combined yarns or composite yarns. Multi-component yarns and processes for their manufacture are described, for example, in U.S. Pat. No. 7,178,323. In the case of the present invention, such yarns would be manufactured of materials that are designed to enhance the thermal conductivity of the end product (e.g., fabric) in which they are employed. For example, in a three-strand multi-component yarn, two of the three strands could be nylon while the third strand might be a copper, silver, carbon nanotube strand, etc.

Other thermal buffering or conductivity enhancements of the fabric 25 may include yarns containing phase change materials. One or more conductive coatings may also be applied to the yarns that make up the fabric, may be applied to the entire fabric, or may be applied to the substrate of a non-woven fabric (e.g., Xymid®). The fabric 25 may also be modified by doping the individual yarns with conductive fillers such as fullerenes or graphene. In other embodiments, conductive wires may be knit or woven into the fabric, or may be spirally wound over elastic fibers.

Figure 3:
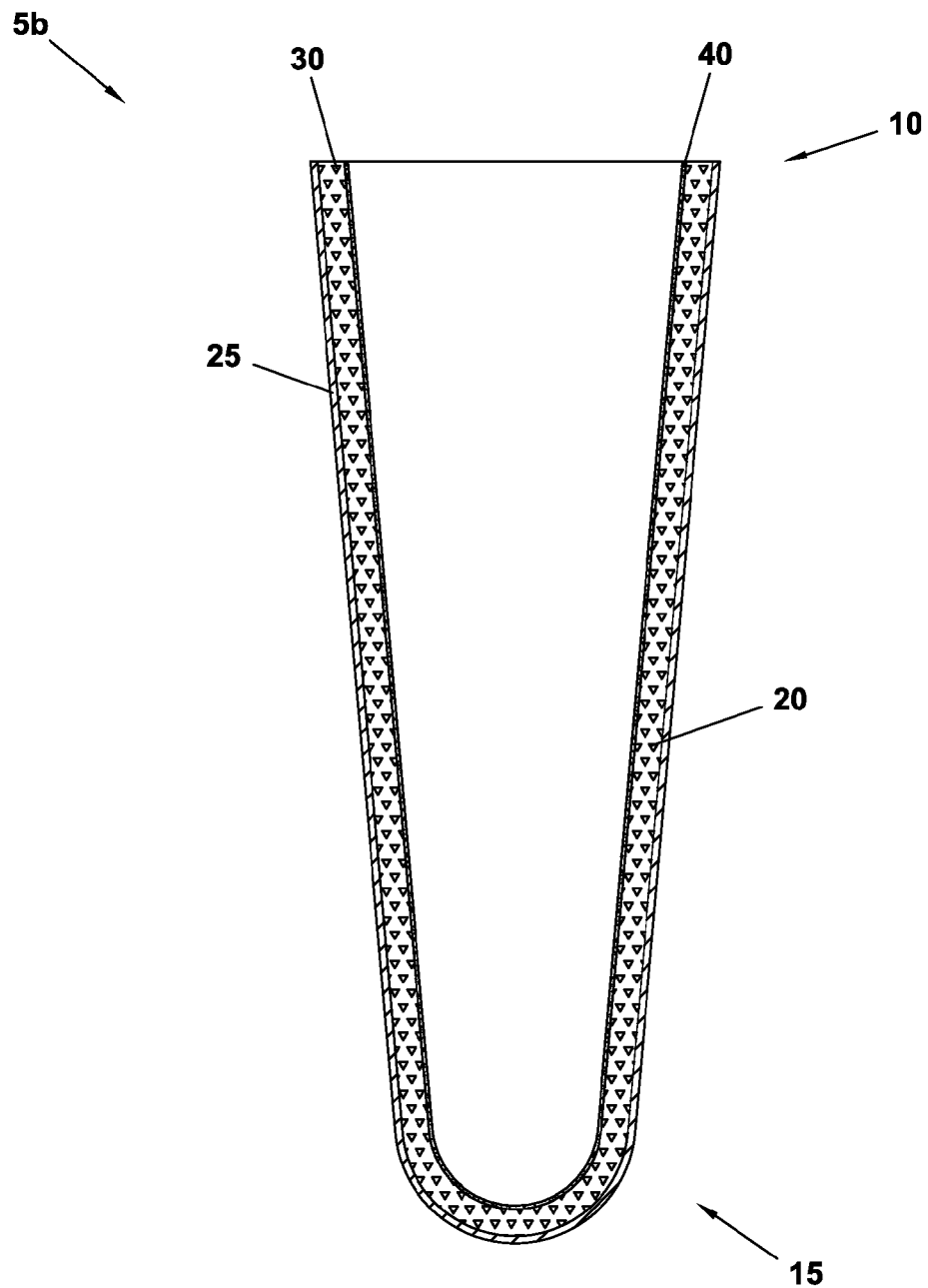
FIG. 3 is a cross-sectional view of another exemplary embodiment of a prosthetic liner of the invention.

An alternate version of the liner 5 of FIG. 1A is depicted in FIG. 3. This exemplary embodiment of the liner 5b is again comprised of a polymeric material 20 having a fabric outer covering 25 and includes enhanced thermal conductivity. However, unlike the exemplary embodiment shown in FIG. 2, this exemplary embodiment further includes a phase change material 40 that is provided in a layer of some thickness over all or part of the liner. As would be understood by one of skill in the art, and as is described in more detail below, a phase change material may be generally defined as a material that is capable of storing and releasing energy (e.g., heat) when the material changes state (e.g., changes from a solid to a liquid, from a liquid to a gas, etc.).

In this exemplary embodiment, the phase change material 40 is located along an area of the liner 5b that will reside near the skin of an amputee's residual limb when the liner is worn so as to most effectively absorb heat from the residual limb and transfer heat away from the residual limb through the polymeric material and fabric of the liner. Consequently, this exemplary embodiment again preferably includes a polymeric material 20 and a fabric 25 with good inherent thermal conductivity or a polymeric material and fabric that has been enhanced in this regard, as shown. For example, the thermal conductivity enhancing techniques described in regard to the polymeric material of the liner of FIG. 2 may again be employed.

Alternatively, it is possible to produce a liner similar to that shown in 5b but without a polymeric material 20 having particularly good thermal conductivity. In such an embodiment, the phase change material 40 would assume the entire role, or at least the majority of the role, in removing heat from the residual limb. Therefore, as long as the phase change material 40 does not become heat-saturated, it should still provide for some amount of cooling effect. In addition to the embodiment of FIG. 3 wherein the phase change material is provided in a layer, other similar embodiments may have instead, or in addition to, a phase change material dispersed within the polymeric material, a localized area(s) (e.g., pocket(s)) of phase change material, etc. In any case, upon removal of the liner 5b from the residual limb, heat will be transferred from the phase change material 40 to the ambient environment.

Figure 4:
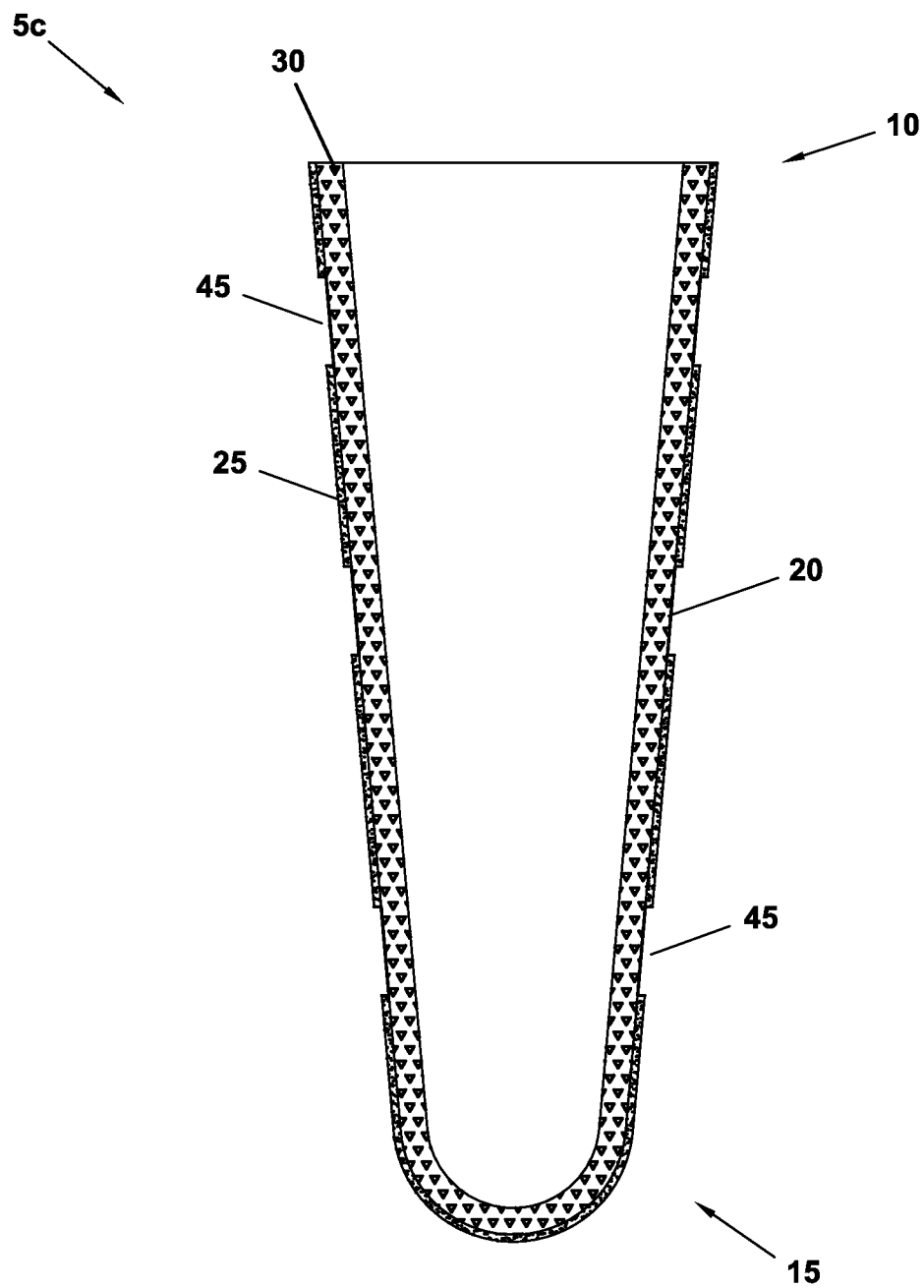
FIG. 4 is a cross-sectional view of another exemplary embodiment of a prosthetic liner of the invention.

Still another exemplary embodiment of a liner 5c of the invention having enhanced thermal conductivity is illustrated in FIG. 4. This exemplary liner 5c is shown to be similar to the liner 5 of FIG. 2, as it is comprised of a polymeric material 20 having a fabric outer covering 25, and the polymeric material 20 is shown to include thermally conductive additives/fillers 30 that are dispersed within the polymeric material. This exemplary liner 5c could also employ a phase change material layer 40 as shown in FIG. 3, could include a phase change material arranged as otherwise described above, or a phase change material in an arrangement such as one or more of the arrangements described in more detail below.

This embodiment of the liner 5c may again include a fabric 25 with good inherent thermal conductivity or a fabric that has been enhanced in this regard. It may also be possible for this embodiment of the liner 5c to include a fabric 25 without particularly good thermal conductivity characteristics or a fabric that has not been enhanced in this regard. This latter possibility is due to the presence of multiple regions of omitted fabric (e.g., voids) 45 that allow for the exposure of the thermal conductivity enhanced polymeric material 20. One or more voids may be present in various embodiments. The voids may be of various size and shape, and may be uniformly or randomly located along the liner 5c.

The voids 45 in the fabric covering 25 preferably permit the exposed areas of polymeric material 20 to contact the interior wall of a prosthetic socket when a liner-covered residual limb is inserted therein. Consequently, the polymeric material 20 is then able to directly transfer heat from the residual limb to the socket without the need to transfer the heat through the fabric covering 25. As should be apparent to one of skill in the art, also employing a naturally thermally conductive fabric or a fabric with enhanced thermal conductivity may further promote heat transfer in such an embodiment.

Figure 5:
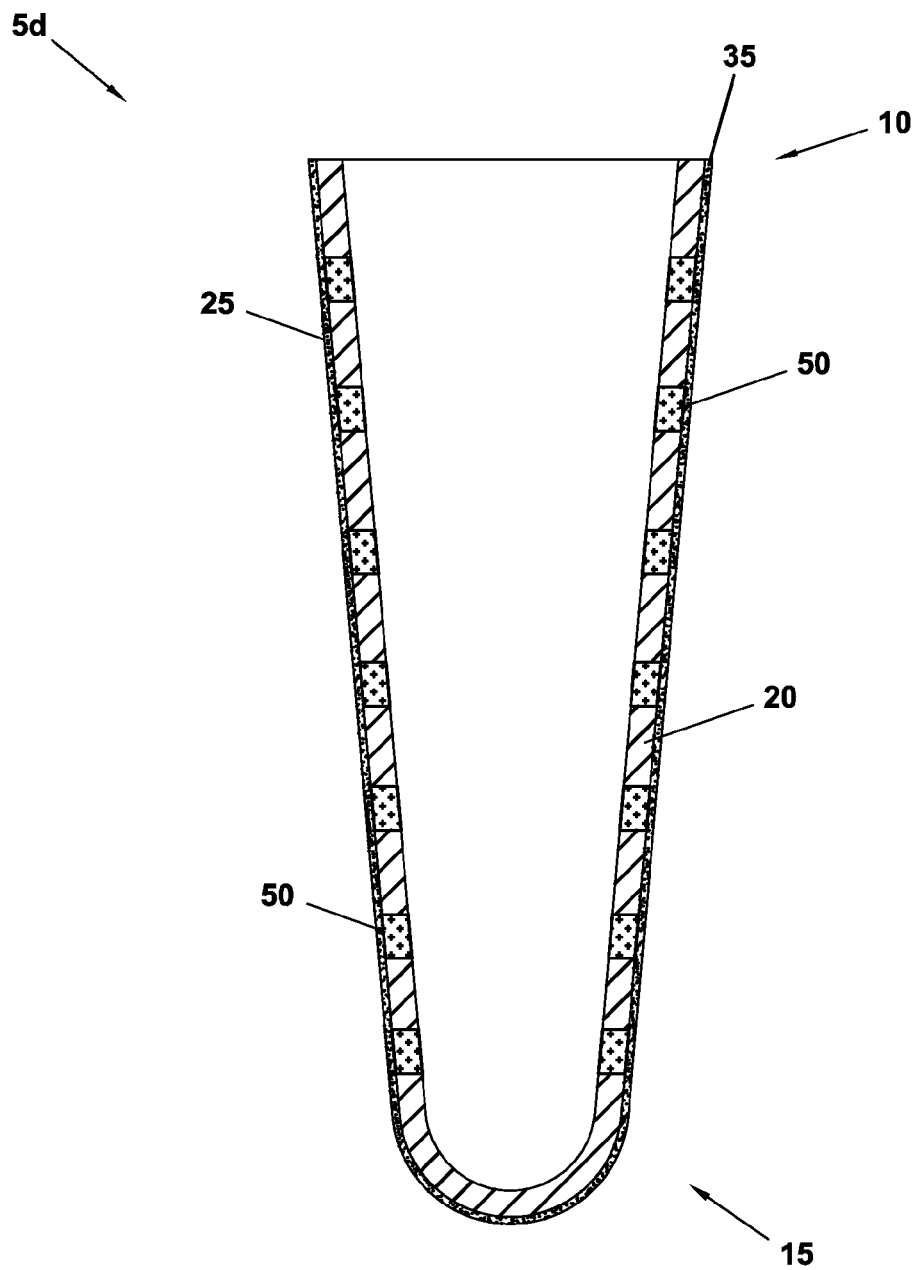
FIG. 5 is a cross-sectional view of another exemplary embodiment of a prosthetic liner of the invention.

Another exemplary embodiment of a liner 5d of the invention having enhanced thermal conductivity is depicted in FIG. 5. Unlike previous embodiments, this embodiment of the liner 5d includes fluid-filled pockets 50 that reside within the polymeric material 20 and help to conduct heat from the residual limb through the liner. One or a plurality of such pockets may be present. The fluid-filled pockets would operate by not only increasing the thermal conductivity of the assembly, but also by facilitating the transfer of heat by convection and other currents induced by the motion of the liner and an associated socket.

Figure 8:
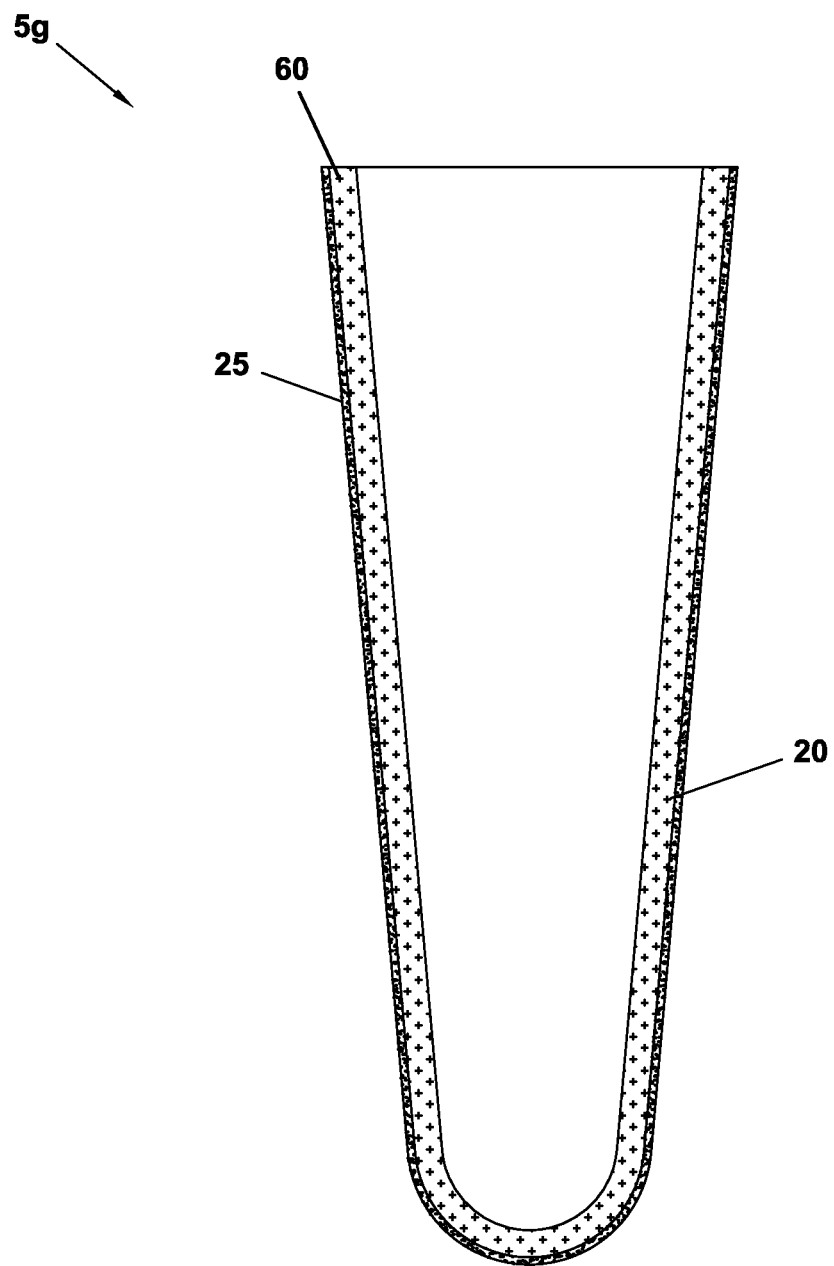
FIG. 8 is a cross-sectional view of another exemplary embodiment of a prosthetic liner of the invention.
Figure 11:
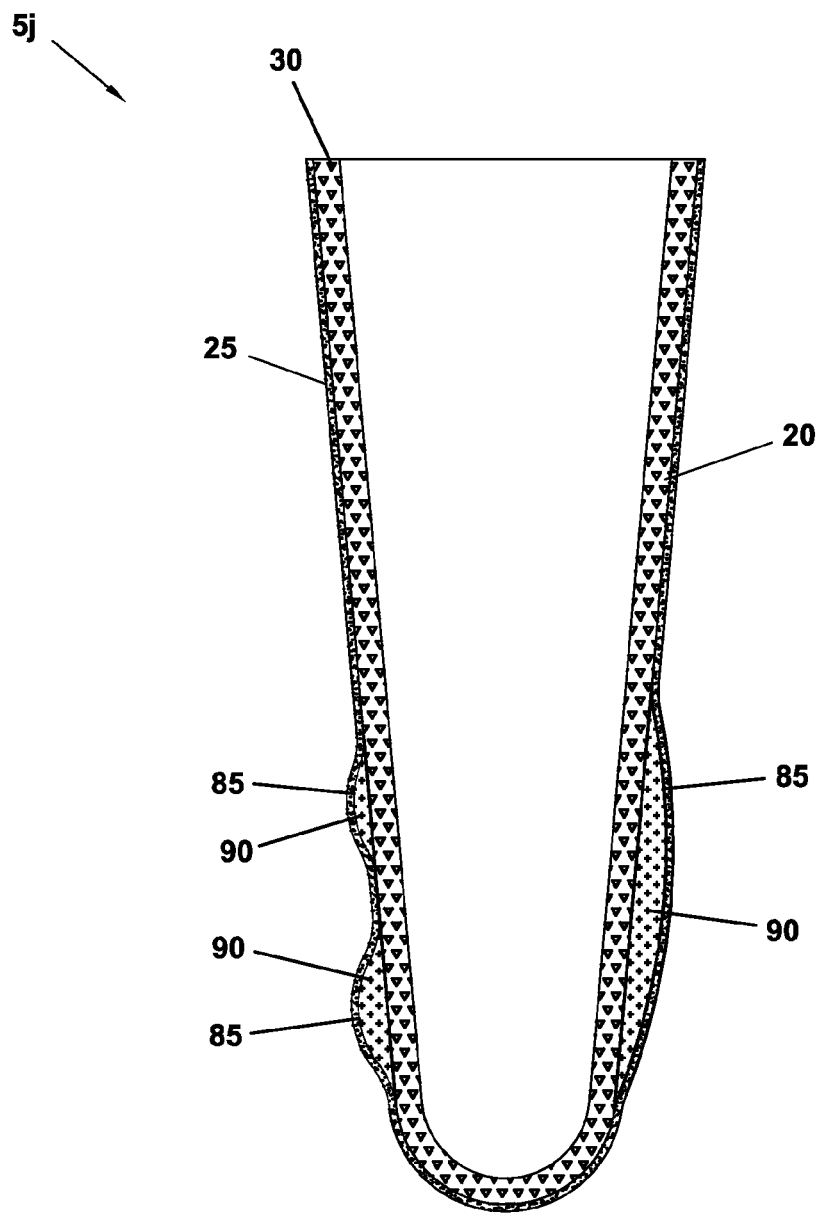
FIG. 11 is a cross-sectional view of another exemplary embodiment of a prosthetic liner of the invention FIG. 12 schematically represents an exemplary embodiment of a prosthetic hard socket of the invention.

As shown, this exemplary embodiment 5d of FIG. 5 may employ a polymeric material that is not provided with enhanced heat transfer characteristics beyond those resulting from use of the fluid-filled pockets 50. Alternatively, the polymeric material 20 may also be provided with additives/fillers as shown in FIGS. 2 and 4 and/or a phase change material provided in a layer as shown in FIG. 3, dispersed within the polymeric material as shown in FIG. 8, and/or provided in localized areas as shown in FIG. 11.

This embodiment of the liner 5d may include a fabric 25 with good inherent thermal conductivity, or a fabric that has been enhanced 35 in this regard, as shown. This embodiment of the liner 5d may again also include a fabric 25 without particularly good thermal conductivity characteristics or a fabric that has not been enhanced in this regard, in which case one or more voids are preferably present in the fabric and located to overlie the fluid filled pockets 50 and to perhaps correspond in size and shape thereto, in a manner similar to that shown and described with respect to FIG. 4.

Figure 6:
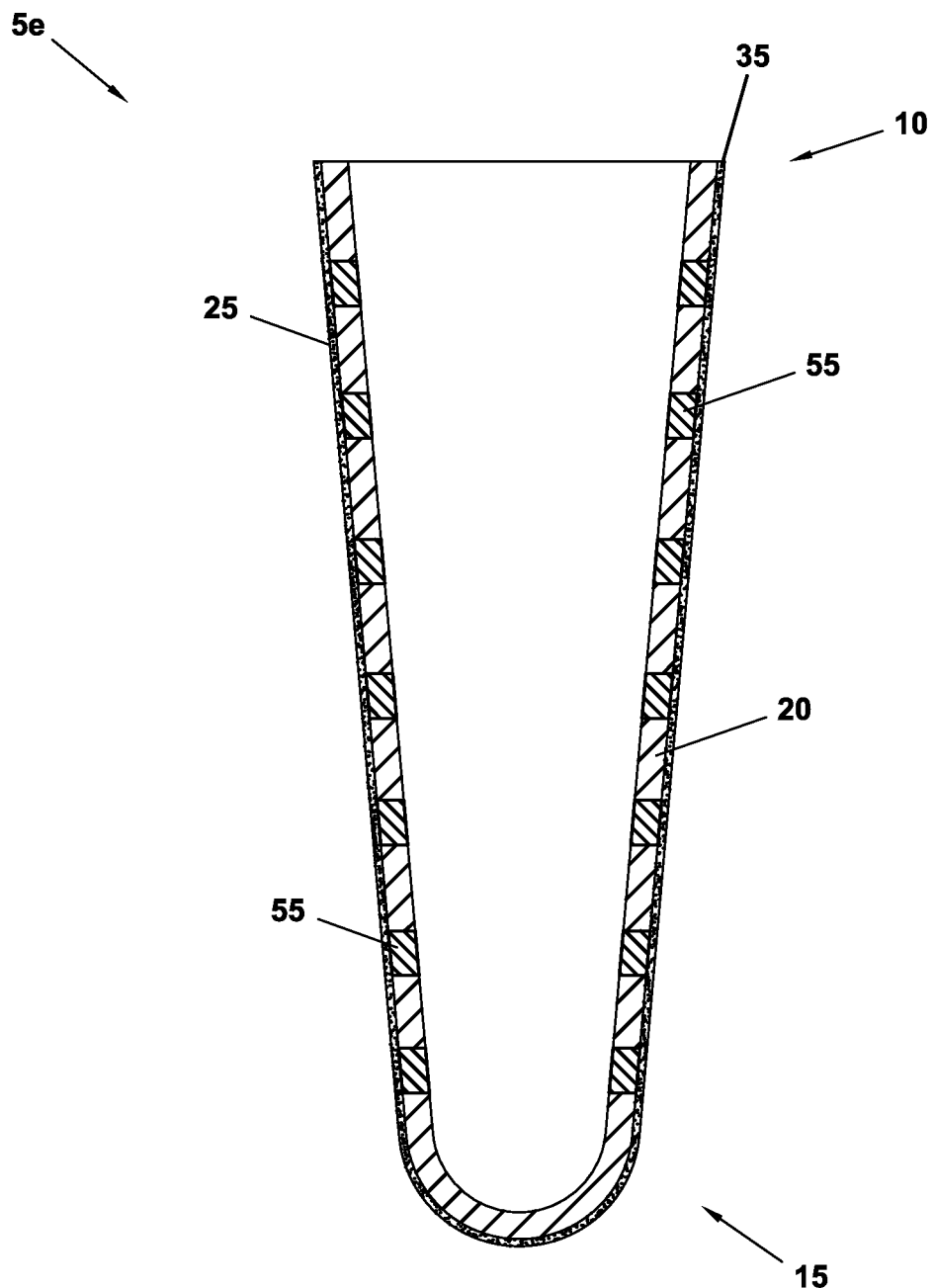
FIG. 6 is a cross-sectional view of another exemplary embodiment of a prosthetic liner of the invention.

In yet another embodiment, which is generally represented in FIG. 6, a liner 5e of the invention may include one or more areas of high thermal conductivity 55 within the polymeric material 20. These area(s) of high thermal conductivity 55 may be comprised of, for example, one or more polymeric materials that are dissimilar to the polymeric material 20 forming the primary portion of the liner, and which exhibit better thermal conductivity.

As shown, this exemplary embodiment 5e of FIG. 6 may employ a primary polymeric material 20 that is not provided with enhanced heat transfer characteristics beyond those resulting from use of one or more areas of high thermal conductivity 55 within the polymeric material. Alternatively, the polymeric material 20 may also be provided with thermally conductive additives/fillers as shown in FIGS. 2 and 4 and/or a phase change material provided in a layer as shown in FIG. 3, dispersed within the polymeric material as shown in FIG. 8, and/or provided in localized areas as shown in FIG. 11.

This embodiment of the liner 5e may include a fabric 25 with good inherent thermal conductivity, or a fabric that has been enhanced 35 in this regard, as shown. This embodiment of the liner 5e may again also include a fabric 25 without particularly good thermal conductivity characteristics or a fabric that has not been enhanced in this regard, in which case one or more voids are preferably present in the fabric as shown in FIG. 4 and described above. In this case, the voids in the fabric covering 25 would preferably correspond in location and perhaps in size and shape with the one or more areas of high thermal conductivity 55 within the polymeric material 20, in a manner similar to that shown and described with respect to FIG. 4.

Figure 7:
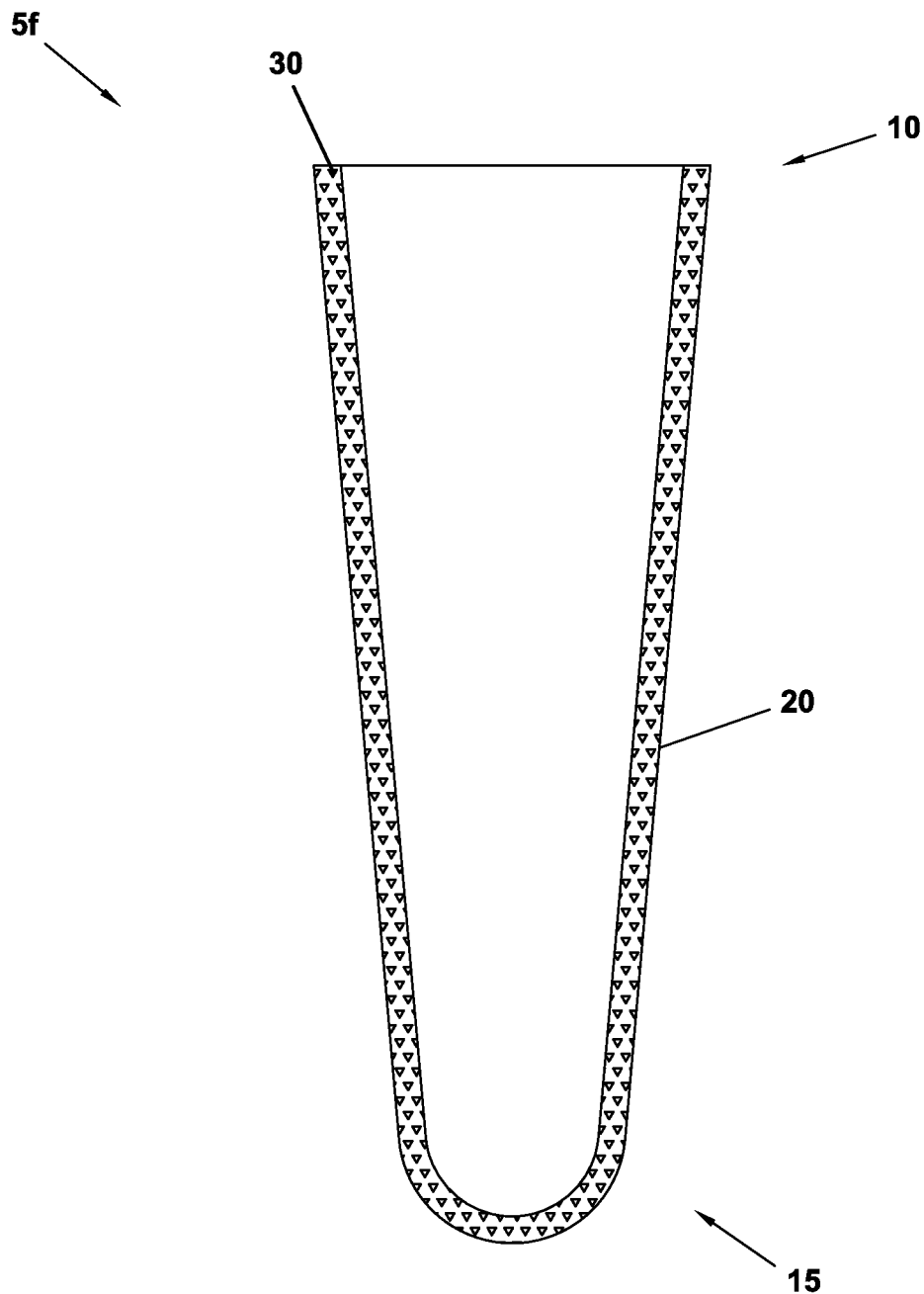
FIG. 7 is a cross-sectional view of another exemplary embodiment of a prosthetic liner of the invention.

Another embodiment of a liner 5f of the invention can be observed in FIG. 7. As shown, this liner 5f is comprised of a polymeric material 20 without a fabric exterior. Consequently, the polymeric material 20 will typically be in contact with the skin of a residual limb when the liner is worn and will also typically reside against interior of a prosthetic socket when the liner is used with a prosthetic limb, although this may not be the case in all embodiments. In a variation of this embodiment, a phase change material layer may be located along the interior surface of the polymeric material so as to reside near the skin of an amputee's residual limb when the liner is worn, may be dispersed within the polymeric material as shown in FIG. 8, and/or may be provided in localized areas as illustrated in FIG. 11. The phase change material(s) acts to absorb and store heat generated by the residual limb and, at least to some extent, and may assist with the transfer of heat therefrom to the polymeric material layer 20 in the manner described above with respect to the embodiment of FIG. 3.

The polymeric material portion of this embodiment 5f may be comprised of, without limitation, any one of the polymeric materials or combinations of polymeric materials described above. For example, the polymeric material may be silicone. However, because such polymeric materials are typically very tacky, rolling them onto a residual limb without the exterior fabric layer would be difficult without the inclusion of some type of lubricant on the outer liner surface.

Therefore, a lubricious outer coating may be applied to the exterior of the liner 5f such as by spraying or wiping the liner exterior with alcohol or a similarly suitable substance. This is a less than optimal solution, however, as it creates an additional donning step for the amputee and at least certain lubricants can be messy to apply and remove. Consequently, variations of the fabric-free liner 5f may include an exterior surface that is treated to produce a long-term or permanent reduction in the coefficient of friction thereof. Treatment methods useable in this regard may include the spraying on or vapor deposition of any of a number of friction reducing materials, which would be familiar to one of skill in the art and need not be discussed in detail herein (e.g., parylene).

As with at least certain other exemplary liner embodiments described herein, this embodiment of the liner 5f includes a polymeric material 20 that has been modified by the inclusion therein of thermally conductive additives/fillers 30 that are preferably dispersed within the polymeric material. Suitable additives/fillers 30 may again include, without limitation, fullerenes such as carbon nanotubes; graphene platelets; boron nitride platelets; boron nitride fibers; boron nitride spherical powder; boron nitride agglomerates; diamond powder; graphite fibers; powders of silver, copper, gold and aluminum oxide; aluminum powder; and various combinations of two or more such additives/fillers.

As can be understood from the foregoing descriptions of exemplary embodiments, liners according to the invention may be highly heat absorbing instead of, or in addition to, possessing enhanced heat transfer capabilities. Generally, the heat absorbing capability of a liner of the invention is enhanced through the use of a phase change material. As briefly explained above, phase change materials are materials that store and release energy (e.g., heat) when the material changes state. The change in state occurs at some transition temperature, which is generally known. For example, it may be known that a given phase change material transitions from a solid to a liquid at about some particular temperature. The same phase change material will also have a transition temperature associated with the reverse process of reverting from a solid back to a liquid. Different phase change materials may have significantly different transition temperatures. For example, water transitions from a solid to a liquid, or vice versa, at roughly 32° F., whereas other materials may make a similar phase transition at a much higher temperature.

Various types of phase change materials may be employed in embodiments of the invention as long as the associated transition temperature thereof is within a usable range. These material may include for example, positive temperature organics (e.g., waxes, oils, fatty acids), salt hydrates, and even solid-to-solid phase change materials (e.g., clathrates). (See also, e.g., A review on phase change energy storage: materials and applications, Mohammed M. Farid, Amar M. Khudhair, Siddique Ali K. Razack, and Said Al-Hallaj, Energy Conversion and Management 45 (2004) 1597-1615, for a discussion of possible exemplary phase change materials).

The transition temperature should be considered when selecting a phase change material for use in a prosthetic or orthotic device of the invention. Ice, for example, may be an attractive phase change material from the standpoint of its ability to provide significant cooling to a residual limb. However, the transition temperature of ice is far too low to generally be comfortably or safely used in a prosthetic liner or suspension sleeve. Rather, consideration should be given to the range of temperatures that are likely to be generated within a prosthetic liner and experienced by the wearer thereof. It has been found through testing, for example, that most amputees begin to feel uncomfortable when their residual limb temperature exceeds approximately 90° F. However, this temperature may vary based on the individual amputee, and also perhaps based on their activity level and/or the ambient environment. Therefore, phase change materials having a transition temperature that falls within some range of temperatures that may or are likely to be experienced by a residual limb may be appropriate for a prosthetic liner application. For example, it is believed that phase change materials with a transition temperature in the range of about 75° F. to 95° F. would be generally viable for use in prosthetic liner embodiments of the invention that would be suitable for the vast majority of amputees without the need for further thermal regulation. An even wider range of materials becomes usable if other modes of thermal regulation are utilized. It is also possible that phase change materials with transition temperatures outside of the above-stated range may also be usable in certain situations.

It is also noted that the solid-to-liquid transition temperature for a given phase change material is not necessarily the same as the liquid-to-solid transition temperature. In fact, it has been found that the difference between these transition temperatures can sometimes be significant. Consequently, it may at least advisable depending on the given situation, to consider how closely the liquid-to-solid transition temperature matches the solid-to-liquid transition temperature—as it is only during a phase change that a phase change material can store or release heat with maximum efficiency.

It should be further understood that, while exemplary prosthetic and/or orthotic embodiments of the invention that employ phase change materials are described herein for purposes of illustration specifically with respect to the cooling capabilities thereof, the scope of the invention is not limited to the use of phase change materials only for cooling. Rather, just as the selection of a phase change material with a melting point near the upper limit of a patient's comfort range can buffer against high temperatures, it is to be understood that a phase change material can instead be used to buffer against low temperatures. For example, in a heating application, a phase change material may be selected with a transition temperature that is instead near the bottom of a patient's comfort range. As such, similar techniques and designs can also be used to buffer against cold temperatures.

One exemplary embodiment of a liner 5g having enhanced heat absorption capabilities is shown in FIG. 8. This exemplary embodiment of the liner 5g is again comprised of a polymeric material 20 having a fabric outer covering 25. However, unlike the previously described exemplary liner embodiments, this exemplary liner 5g includes a phase change material 60 that is dispersed substantially throughout the polymeric material 20 of the liner. The polymeric material 20 and/or the fabric 25 of the liner 5g may also have good inherent thermal conductivity or may include high thermal conductivity additives/fillers 30 (as shown) or be otherwise enhanced for maximized heat transfer, such as in any manner described above with respect to the embodiments of FIGS. 2-7.

Figure 9:
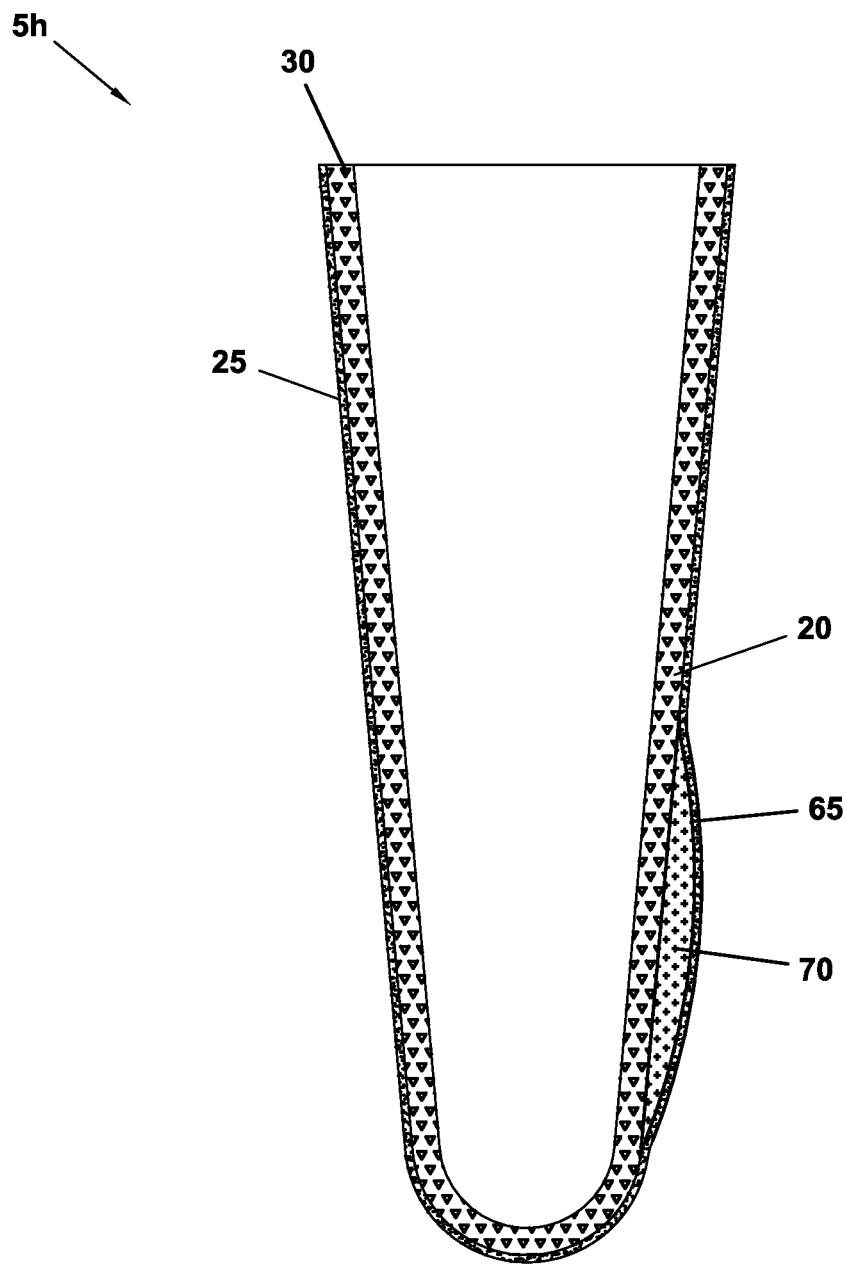
FIG. 9 is a cross-sectional view of another exemplary embodiment of a prosthetic liner of the invention.

In other embodiments, a bladder or similar container of a phase change material, such as a wax-type phase change material, may be present. Such an exemplary liner embodiment is depicted in FIG. 9. This exemplary embodiment of the liner 5h is again comprised of a polymeric material 20 having a fabric outer covering 25. However, unlike the previously described exemplary liner embodiments, this exemplary liner 5g includes a bladder 65 of phase change material 70 that is incorporated into the liner 5h. For example, the bladder 65 may be attached to the fabric 25 of the liner before molding, and the polymeric material 20 may then be molded around and over the bladder such that it becomes integral to the liner 5h. As with the liner embodiment 5g of FIG. 8, the polymeric material 20 and/or the fabric 25 of this liner 5h may also have good inherent thermal conductivity or may include high thermal conductivity additives/fillers 30 (as shown) or be otherwise enhanced for maximized heat transfer, such as in any manner described above with respect to the embodiments of FIGS. 2-7.

Figure 10:
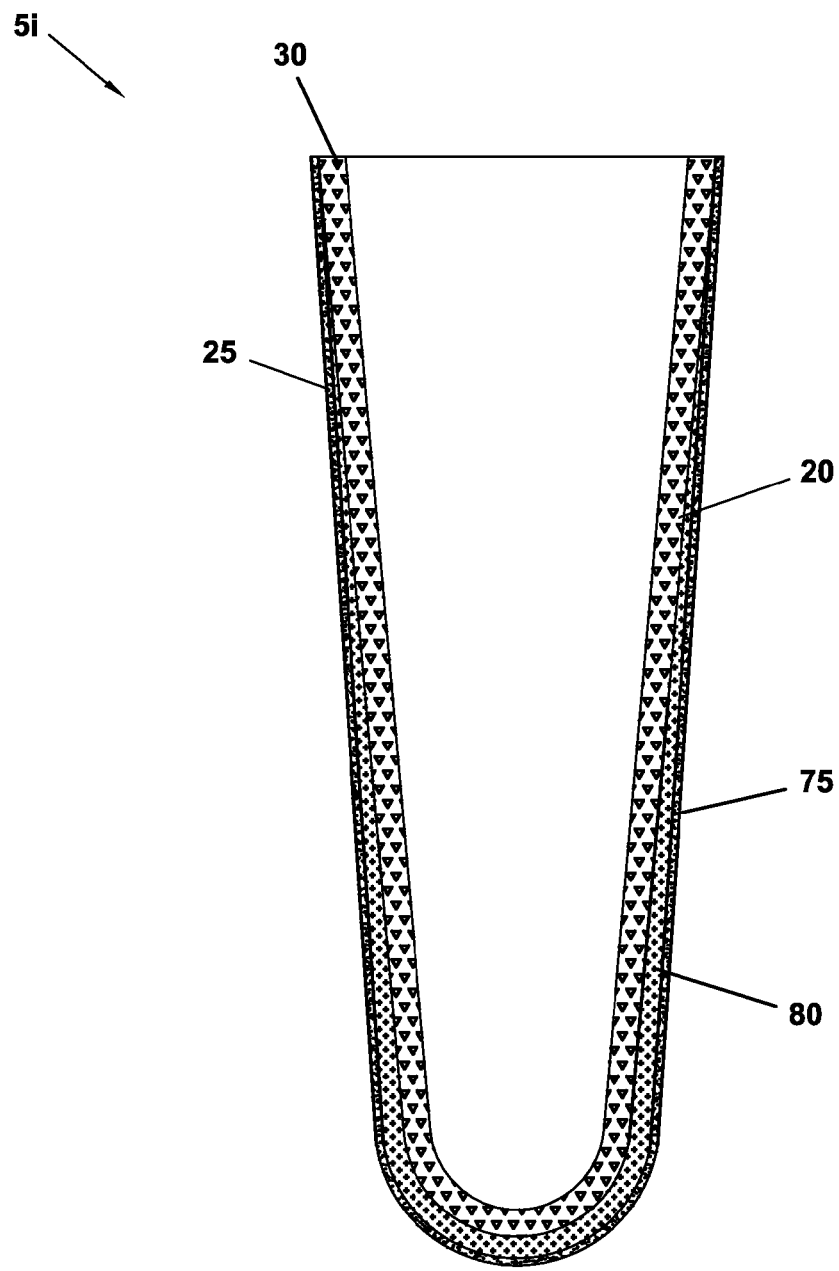
FIG. 10 is a cross-sectional view of another exemplary embodiment of a prosthetic liner of the invention.

Alternatively, another embodiment of a liner 5i with enhanced heat absorption capabilities is represented in FIG. 10. This exemplary embodiment of the liner 5i is again comprised of a polymeric material 20 having a fabric outer covering 25. However, unlike the previously described exemplary liner embodiments, this exemplary liner 5i includes a bladder 75 of phase change material 80 that covers a substantial portion of the liner. As with the liner embodiments 5g-5h of FIGS. 8-9, the polymeric material 20 and/or the fabric 25 of this liner 5i may also have good inherent thermal conductivity or may include high thermal conductivity additives/fillers 30 (as shown) or be otherwise enhanced for maximized heat transfer, such as in any manner described above with respect to the embodiments of FIGS. 2-7.

Yet another embodiment of a liner 5j with enhanced heat absorption capabilities is represented in FIG. 11. This exemplary embodiment of the liner 5j is again comprised of a polymeric material 20 having a fabric outer covering 25. In this exemplary embodiment, a plurality of localized bladders 85 containing a phase change material 90 are used. As with the liner embodiment 5g-5i of FIGS. 8-10, the polymeric material 20 and/or the fabric 25 of this liner 5j may also have good inherent thermal conductivity or may include high thermal conductivity additives/fillers 30 (as shown) or be otherwise enhanced for maximized heat transfer, such as in any manner described above with respect to the embodiments of FIGS. 2-7.

An additional exemplary embodiment of a liner with enhanced heat absorption capabilities includes a phase change material with a phase transition temperature that is lower than the typical temperatures experienced within a prosthetic liner during use by an amputee. For example, and without limitation, the phase transition temperature may be about 60° F. At this temperature, the phase change material will always reside in a liquid state when the liner is in use.

Testing has shown that silicone material that includes a phase change material in a liquid state has different mechanical properties than when an included phase change material is a solid. Testing has specifically revealed that that when the phase change material is in a liquid state, the hardness of the silicone is much less (i.e., the silicone is much softer) than when the phase change material is solid, yet the creep value is similar to that of a harder silicone. Consequently, including a liquid state phase change material in the silicone polymeric material of a liner may impart desirable comfort properties to the silicone without the detrimental effects on the mechanical properties typically seen when attempting to formulate a softer silicone.

When any liner embodiment exhibiting enhanced heat absorption capabilities according to the invention is worn, the phase change material(s) present therein absorbs heat generated by the residual limb over which the liner is donned. As described above, the phase change material(s) possess a latent heat capacity that is sufficient to permit absorption of this heat over some given temperature range with no or a only a minimal resulting rise in the localized temperature. The heat absorbed by the phase change material(s) of such a liner embodiment may be subsequently released when the liner is later removed from the residual limb.

Liners of the invention are preferably used in conjunction with a prosthetic socket. It has been discovered through examination that most commercially available or otherwise conventionally produced prosthetic sockets—such as carbon fiber prosthetic sockets—exhibit very poor thermal conductivity primarily due to a very high resin to reinforcing fiber ratio. For example, it has been discovered that existing prosthetic sockets may have an resin-to-reinforcing fiber ratio as high as about 80:20. While other resin-to-reinforcing fiber ratios certainly also exist, the orthotics and prosthetics industry appears to use a far higher ratio of resin to reinforcing fiber (or other reinforcing material) on average than is used by other industries that also produce reinforced composite structures.

It has also been determined that by reducing the amount of resin and/or increasing the amount of reinforcing fiber used, the thermal conductivity of a typically constructed prosthetic socket may be increased beyond normal levels without adversely affecting the strength of the socket. Consequently, a most basic method of increasing the thermal conductivity of a typically constructed prosthetic socket may be to simply optimize the resin-to-reinforcing fiber ratio.

Figure 12:
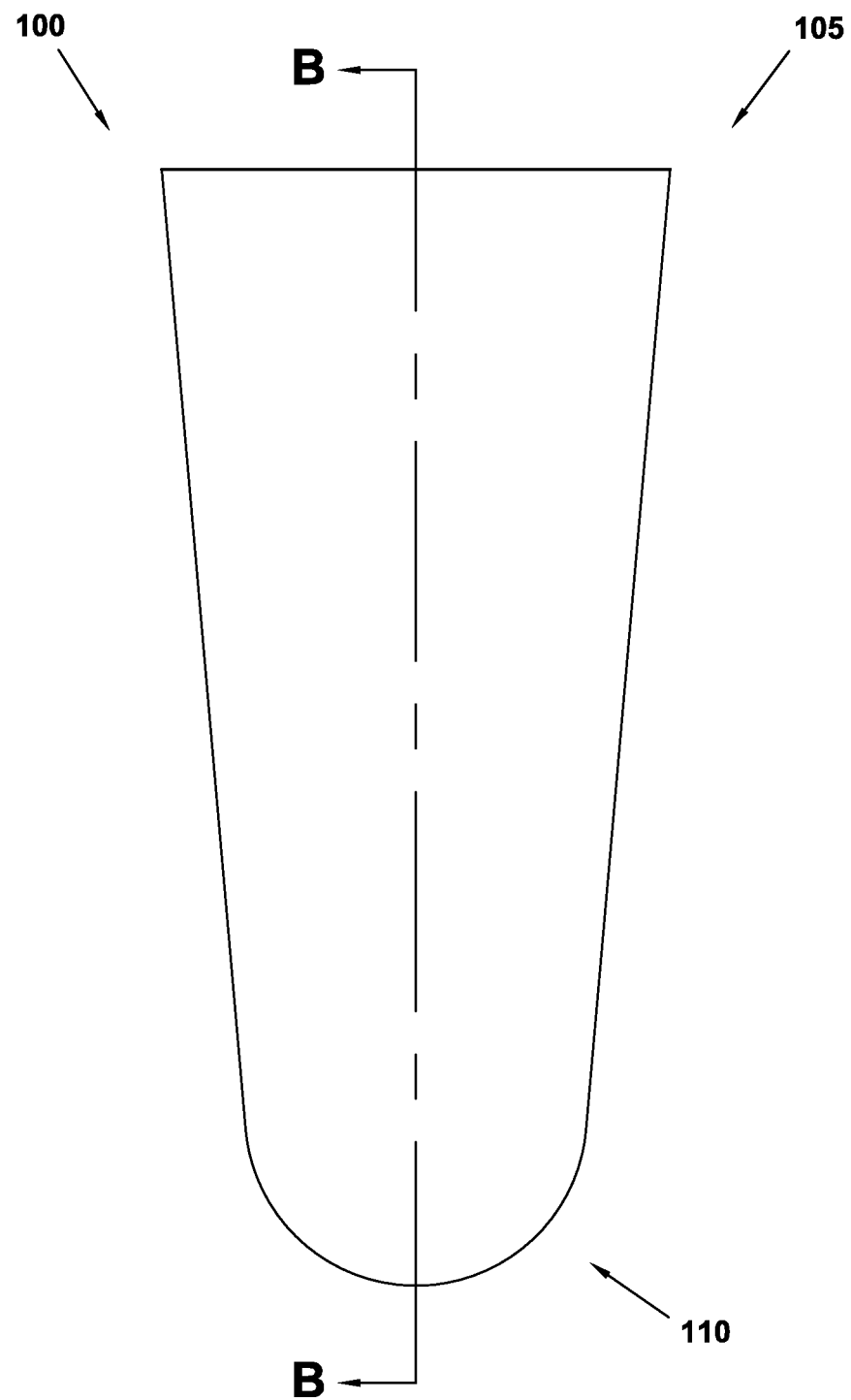

The foregoing commentary notwithstanding, it should be understood that even a prosthetic socket manufactured with an optimized resin-to-reinforcing (e.g., carbon) fiber ratio may still be provided with further enhanced thermal conductivity according to the invention. An exemplary embodiment of such a prosthetic socket 100 is generally represented in FIG. 12. As shown, the prosthetic socket 100 includes an open end 105 for permitting insertion of a liner-covered residual limb (e.g., a liner-covered residual leg), and a closed end 110 opposite the open end.

Figure 13:
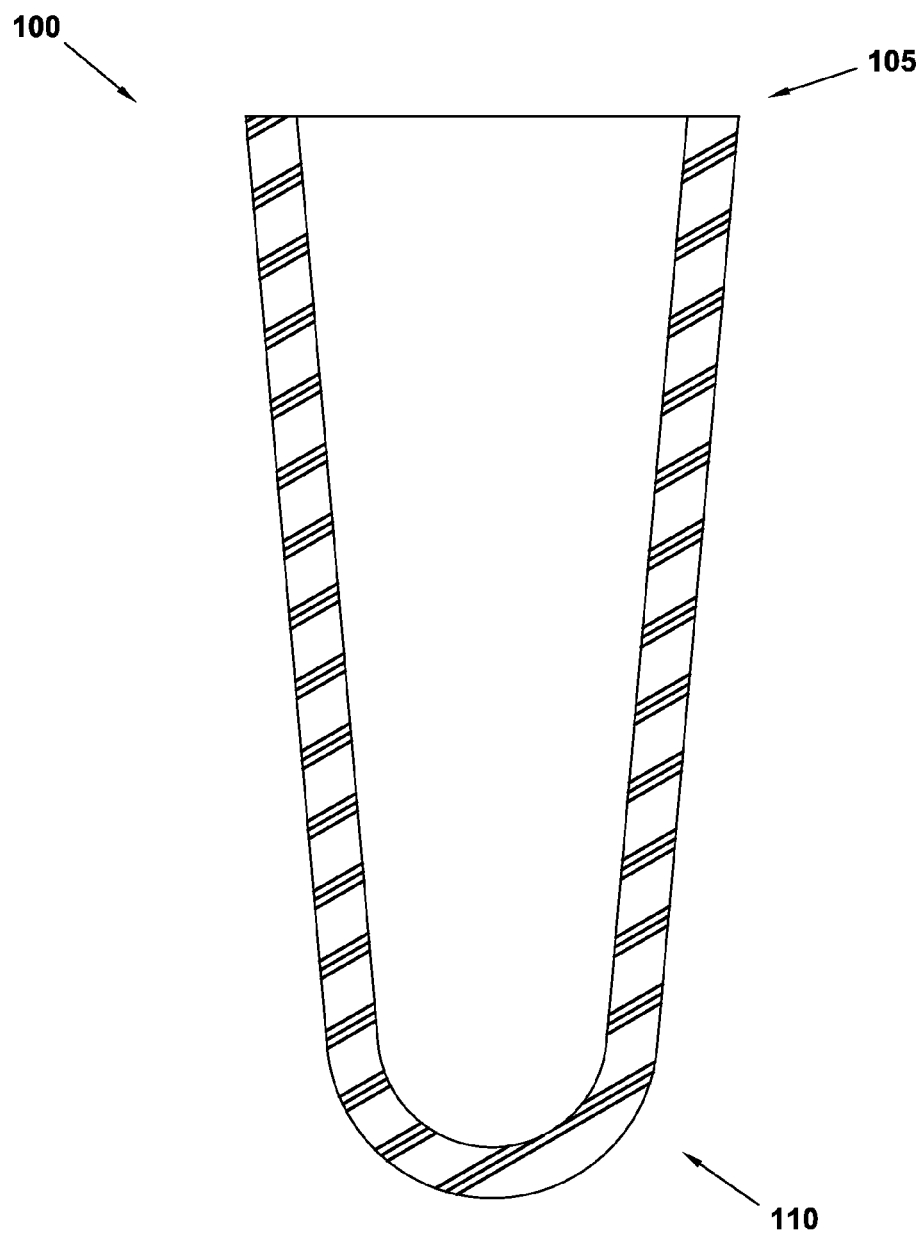
FIG. 13 is a cross-sectional view of an exemplary embodiment of a prosthetic hard socket of the invention.

A first cross-sectional view of the prosthetic socket 100 of FIG. 12 can be observed in FIG. 13. As with at least many of the liner embodiments of the invention, it is also preferred that prosthetic sockets used according to the invention exhibit enhanced thermal conductivity so as to further effectuate the transfer of heat away from the residual limb residing therein. In this regard, the material used to construct the prosthetic socket 100 may be a thermoformable or laminatable material that exhibits good inherent thermal conductivity—as illustrated in FIG. 13.

Alternatively, a prosthetic socket with enhanced thermal conductivity 100b may be constructed via an additive manufacturing technique such as for example, selective laser sintering (SLS). In this case, a material blend containing thermoplastics such as Nylon 11 or Nylon 12 and thermally conductive additives, lends itself well to socket construction. One such commercially available packed Nylon 12 product is Alumide, which is polyamide and aluminum powder resin blend available from the EOS of North America, Inc. in Novi, Mich.

Figure 14:
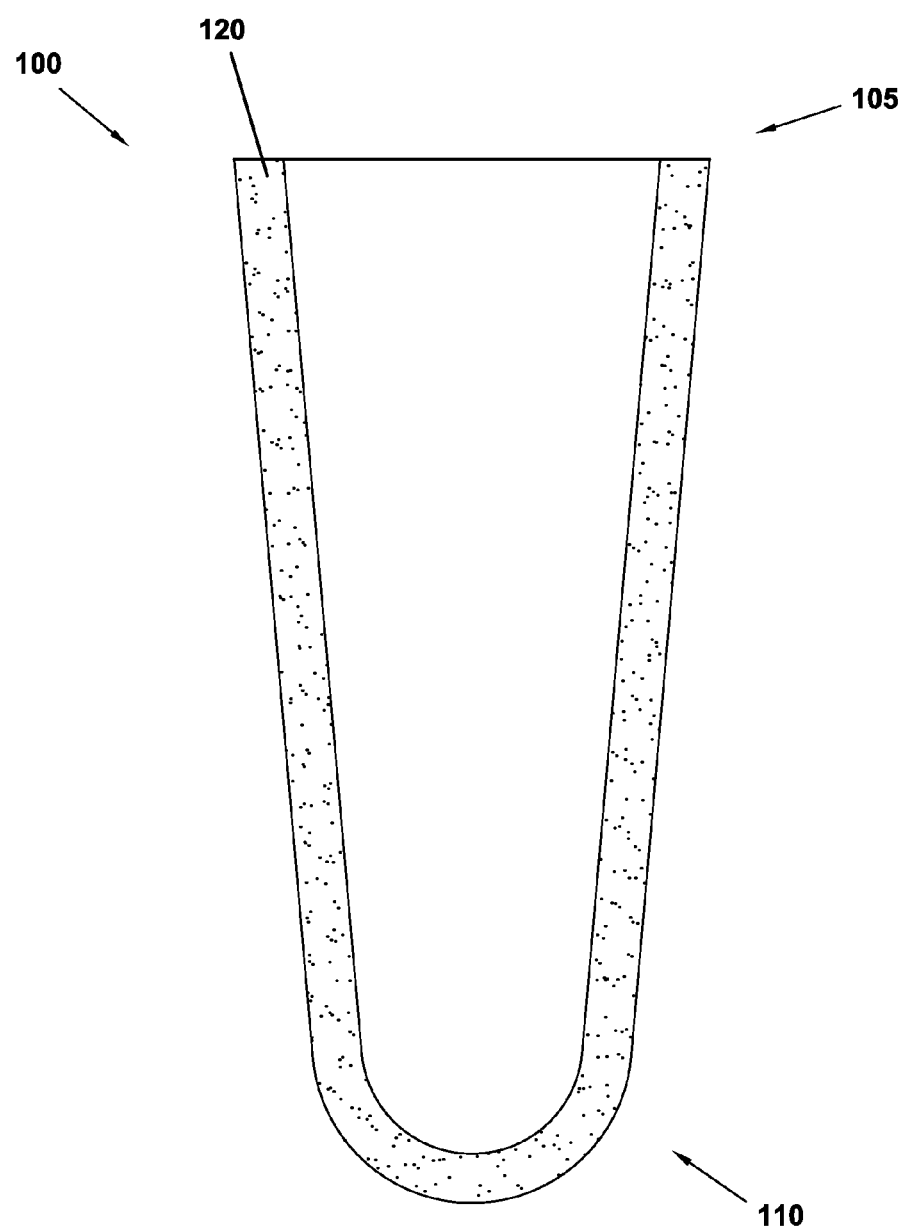
FIG. 14 is a cross-sectional view of another exemplary embodiment of a prosthetic hard socket of the invention.

The base material used to produce any prosthetic socket of the invention, including a base material that already exhibits good inherent thermal conductivity, may also be doped with or otherwise made to include a highly thermally conductive additive/filler 120. Such an exemplary embodiment of a prosthetic socket is generally depicted in FIG. 14.

A number of such potentially usable additives/fillers 120 exist. For example, and without limitation, the material used to construct the thermally conductive prosthetic socket 100b may be doped with additives/fillers 120 such as fullerenes; graphene; boron nitride fibers and platelets; boron nitride spherical powder; boron nitride agglomerates; diamond powder; graphite fibers; powders of silver, copper, gold and aluminum oxide, and aluminum powder.

A phase change material may also be dispersed within the socket material to provide for enhanced heat absorption capabilities. Alternatively, or in addition to the use of a dispersed phase change material, a phase change material may be applied to the socket in a layer that lies along or near the interior socket wall.

Figure 15:
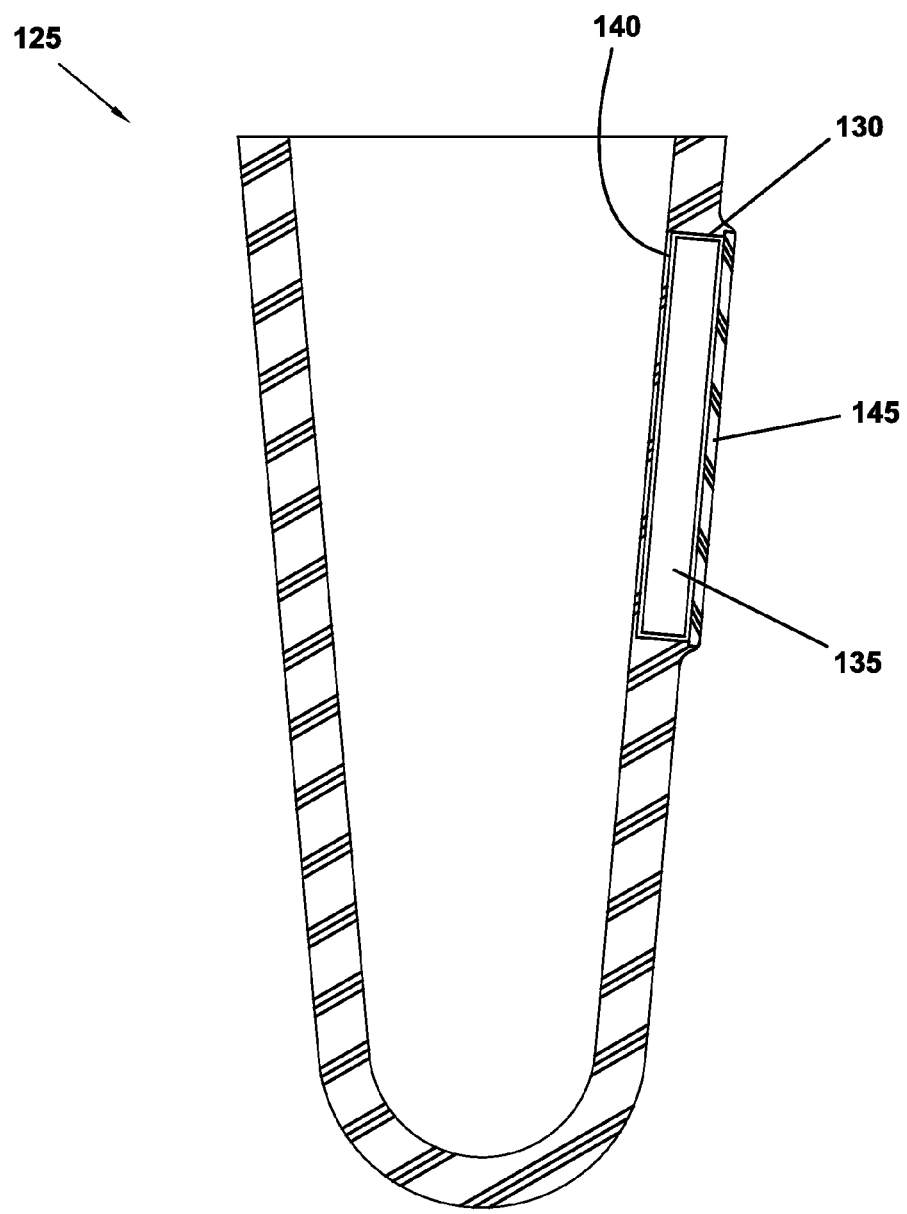
FIG. 15 is a cross-sectional view of another exemplary embodiment of a prosthetic hard socket of the invention.

Another prosthetic socket embodiment with enhanced heat absorption capabilities may employ a phase change material having a melting point below a given average prosthetic socket interior temperature at which an amputee will start to perceive discomfort: either directly from heat, or indirectly due to perspiration. As shown in FIG. 15, an exemplary embodiment of such a prosthetic socket 125 may include a packet 130 of such a phase change material 135 in the solid phase, which may be placed into a receiving portion 140 of the prosthetic socket, such as a recess or some type of enclosure. In any event, the packet 130 of phase change material 135 is connected by a heat flow path to the interior of the socket so as to permit socket temperature regulation. In this simple system, it is the thermal properties of the phase change material 135, i.e. the melting temperature of the phase change material, that provides the temperature regulation function. Should the phase change material 135 become heat saturated, replacement of the packet 130 with another packet of phase change material in the solid phase is all that is required to restore full thermal regulation to the system. The receiving portion 140 in the socket may have a door(s) 145 or some other convenient form of access to allow a user to readily exchange a packet of phase change material if necessary.

It should be pointed out that a prosthetic or orthotic device could also utilize a phase change material(s) with a melting point near the temperature where a user would be expected to become uncomfortably cold. In this way, a user could choose between a heating or cooling effect by simply selecting an appropriate phase change material. A user may be provided with different packets of phase change material for this purpose.

In still another exemplary embodiment, a prosthetic socket of the invention may employ a phase change material having a melting point well below the temperature at which an amputee would start to perceive discomfort from excessively high temperatures. By using a phase change material with a low melting point, a large temperature differential would be created between the amputee's residual limb and the phase change material—thus facilitating high heat flows. Because such a phase change material could have a melting point that is sufficiently low to be uncomfortable to a user, such a design may necessitate that the phase change material be insulated from both the user and the environment so as to prevent both unrestrained cooling of the user, and unrestrained absorption of large amounts of heat from the environment.

A heat switch may be provided to actively or passively regulate the heat flow of a prosthetic socket embodiment utilizing a phase change material having such a low melting point. Active control may be implemented by a thermal measurement device such as a thermocouple or thermistor, in communication with a regulation device and an actuator situated to allow the assembly to regulate the position of a thermally conductive path between the interior of the socket and the packet of phase change material. This permits a completion or breaking of the thermal path. Passive control may be accomplished, for example, through the use of bimetallic disks or strips or, alternatively, through a device designed to be actuated by the thermally induced volume change of a material such as paraffin. Such an embodiment would utilize the thermally induced motion or volume change of these materials to complete or break a heat path between the interior of the socket and the packet of phase change material.

Figure 16:
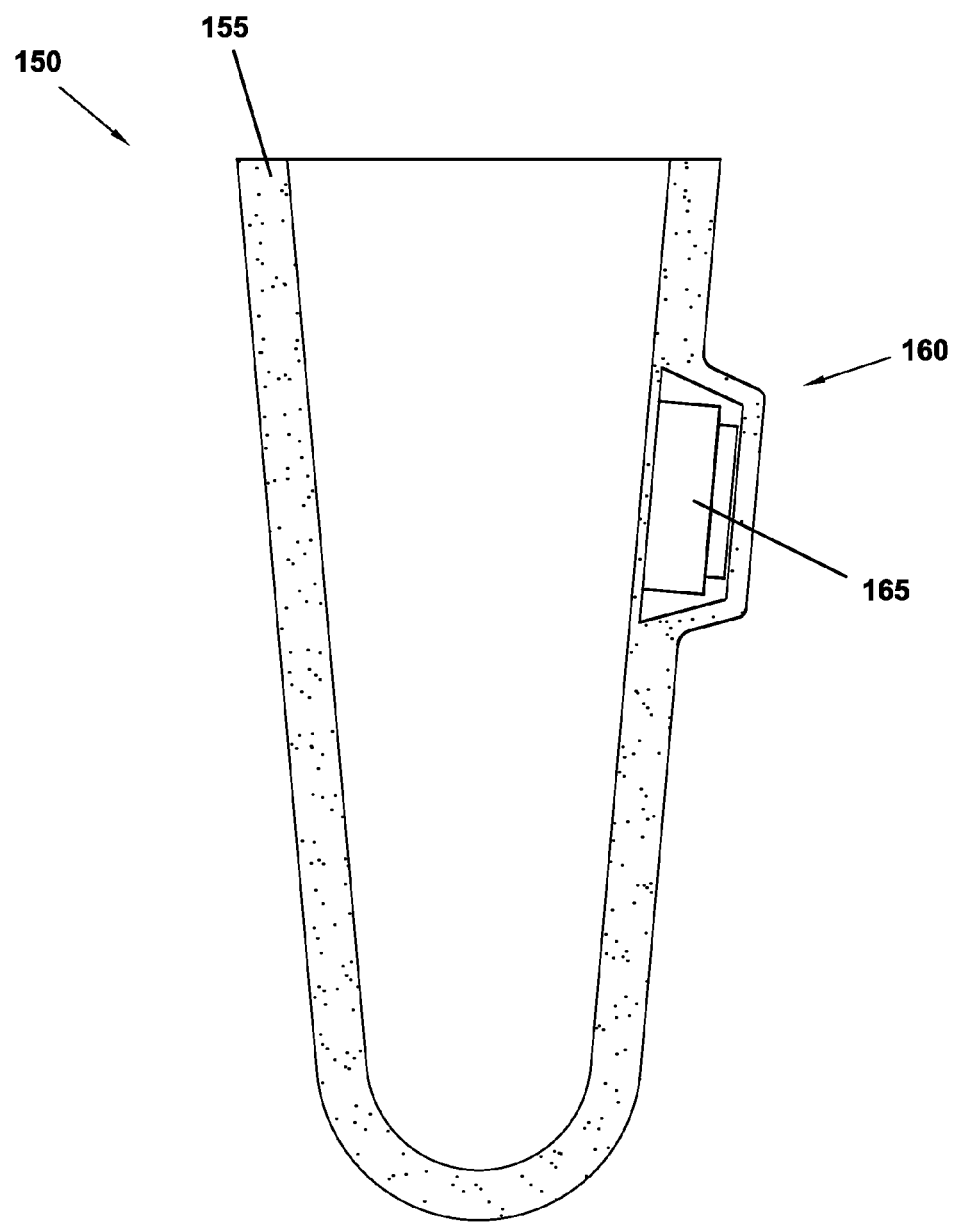
FIG. 16 schematically represents an exemplary embodiment of a prosthetic hard socket of the invention that employs additional passive cooling.

As schematically illustrated in cross-section in FIG. 16, in order to further improve heat transfer through a prosthetic socket it is possible to also employ one or more of a variety of passive heat transfer devices that may be mounted thereto. Passive heat transfer devices may be used in conjunction with a prosthetic socket comprised of a material having inherently good thermal conductivity or with a prosthetic socket comprised of a material that include additives/fillers that improve the heat transfer characteristics of the socket material.

As shown in FIG. 16, an exemplary embodiment of such a prosthetic socket 150 is comprised of a material that include additives/fillers 155 that improve the heat transfer characteristics of the socket material. In other embodiments, the prosthetic socket may be comprised of a material that inherently exhibits good thermal conductivity. A cooling device enclosure 160 is integrated into the socket 150 for the purpose of housing the passive cooling device(s) 165 employed. In other embodiments, a passive cooling device enclosure may be attached to the socket 150. The socket wall may be thinned in the area of the device enclosure (as shown), or it may remain relatively the same thickness as the surrounding socket area.

Such cooling device enclosures may have a variety of shapes and may be of a various sizes.

In the exemplary embodiment shown, the cooling device enclosure is located along a posterior portion of the socket, but may be located elsewhere on the prosthetic socket in other embodiments. It is also possible to employ more than one passive cooling device at more than one location on a given prosthetic socket, in which case more than one cooling device enclosure may also be present.

Passive cooling devices that may be used for this purpose may include, for example, heat sinks, heat pipes, high conductivity metal elements in the form of plates etc., and vapor chambers. Such passive cooling devices would be familiar to one of skill in the art and are commercially available from several sources including, for example, Advanced Cooling Technologies, Inc. and Thermacore, Inc., both located in Pennsylvania.

The passive cooling device(s) 165 are preferably oriented to optimally move heat from a residual limb located in the socket through the socket wall. Heat flow through these high conductivity paths can also be modulated by a device such as a bimetallic actuator (e.g., a Snap Disc thermostat manufactured by Fenwal Controls). Other possible heat flow modulation devices may include, for example, a wax pellet system where an expansive wax pellet is sealed in a small syringe like structure that then changes length when the wax melts and expands; a bimetallic coil; and a gas or liquid bulb system where a bulb is filled with a gas or liquid, and connected to a long tube, often coiled or bent, which tube is straightened by pressure produced within the tube as the gas or liquid is heated and expands. Heat may be transferred from the residual limb through a liner of the invention. Heat transferred by such passive cooling devices may be vented to the ambient environment or, alternatively, may be collected for various purposes such as heating of the residual limb in the case of a subsequent reduction in ambient temperature, etc.

Figure 17:
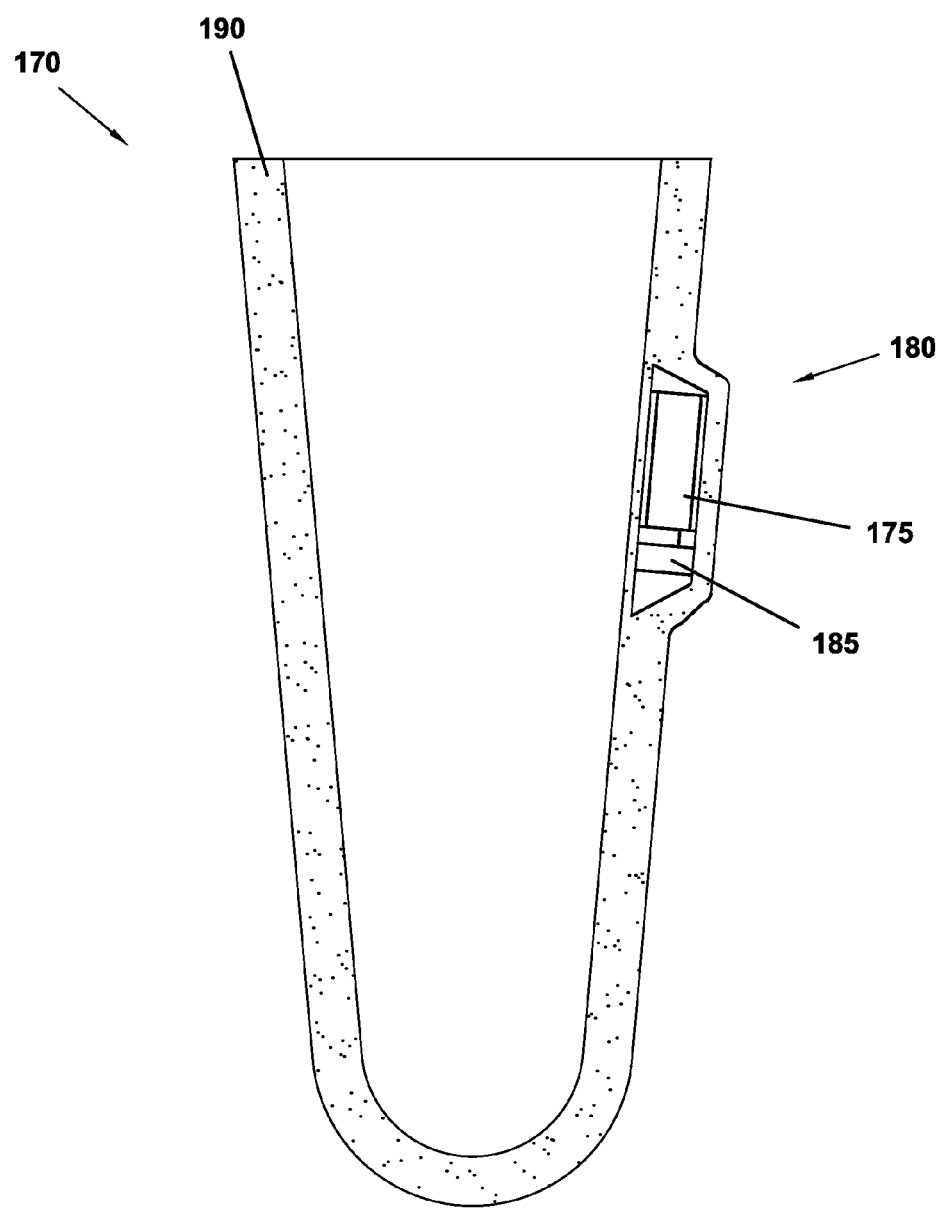
FIG. 17 schematically represents an exemplary embodiment of a prosthetic hard socket of the invention that employs additional active cooling.
Figure 18:
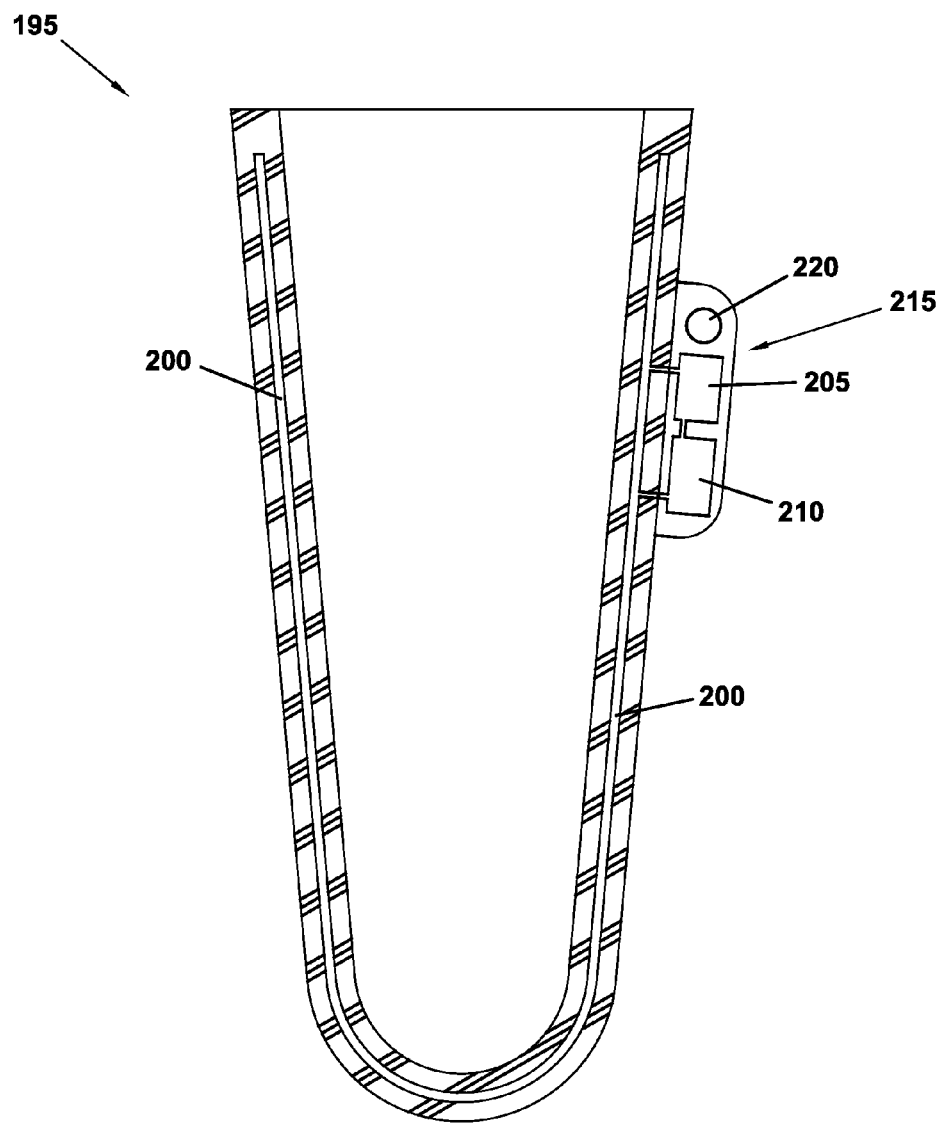
FIG. 18 schematically represents another exemplary embodiment of a prosthetic hard socket of the invention that employs additional active cooling.

As illustrated in FIGS. 17 and 18, it is also possible to employ active cooling mechanisms in order to improve heat transfer through a prosthetic socket. Such active cooling mechanisms may include, without limitation, Peltier devices, cooling channels or cooling tubes through which is circulated a cooling fluid, a fan attached to a heat sink or similar device, or combinations of these devices.

FIG. 17 schematically represents an embodiment of the invention where a Peltier device 175 is used to enhance heat transfer through a prosthetic socket 170. As with the passive cooling device exemplary embodiment shown in FIG. 12, a prosthetic socket embodiment of the invention that employs a Peltier device may also include a device enclosure 180 within which the Peltier device resides. An electrical energy source 185, such as a battery or capacitor, may also be located within the enclosure 180 to power the Peltier device 175. The Peltier device is oriented so as to transfer heat from or to the interior of the socket through the socket wall.

In the exemplary embodiment of FIG. 17, the prosthetic socket 170 is shown to be comprised of a material that include additives/fillers 190 that improve the heat transfer characteristics of the socket material. In other embodiments, the prosthetic socket may be comprised of a material that inherently exhibits good thermal conductivity.

Another embodiment of a prosthetic socket 195 of the invention is schematically illustrated in FIG. 18. In this embodiment, a series of cooling channels 200 are formed within the socket wall and a pump 205 is used to circulate coolant therethrough. Such a prosthetic socket 195 may be formed, for example, using an additive manufacturing process as mentioned above. The pumping method could be one utilizing an electrically-powered pump and an associated power source, such as a battery, or the walking motion of a user may be used to power a mechanical pump.

As the coolant is circulated through the cooling channels 200, it is also passed through a heat exchanger device 210. The heat exchanger device 210 is operative to remove heat from the cooling fluid, as would be well understood by one of skill in the art. A number of known heat exchanger devices may be used for this purpose. As with the passive cooling device of the exemplary embodiment shown in FIG. 16, a prosthetic socket embodiment of the invention that employs a coolant circulating system may also include an enclosure 215 within which may reside the pump 205, the heat exchanger device 210, a power source 220, etc.

In the exemplary embodiment of FIG. 18, the prosthetic socket 195 is shown to be comprised of a material that inherently exhibits good thermal conductivity. In other embodiments, the prosthetic socket may be comprised of a material that includes additives/fillers which improve the heat transfer characteristics of the socket material.

Hybrid prosthetic socket cooling embodiments according to the invention are also possible. Such embodiments may combine both passive and active cooling elements into a single cooling system. One such hybrid embodiment includes an array of heat pipes that are embedded within the wall of a prosthetic socket. For example, the array of heat pipes may be vertically oriented within the socket wall. The heat pipes may be may be restricted to a given area of the socket, such as a posterior area.

The heat pipes are provided to transfer heat from the socket interior through the socket wall and to the atmosphere. Preferably, one end (the cooling end) of the heat pipes is placed in communication with an externally located heat sink for this purpose. The heat sink may be provided in the form a plate or bar, such as a plate or bar that extends in a circumferential direction around some portion of the socket exterior so as to communicate with the proper end of each heat pipe.

The heat sink is preferably comprised of a material that has a high coefficient of thermal conductivity, as would be understood by one of skill in the art. In exemplary embodiments, the heat sink is comprised of a metal, such as aluminum, but the use of other heat sink materials is possible in other embodiments.

In order to cool a prosthetic socket using a heat pipe array and heat sink arrangement such as that described above, it is necessary that the temperature of the heat sink be less than the temperature of the heat pipes. In such a case, the heat pipes will transfer heat from the warm socket wall to the heat sink. Therefore, exemplary embodiments of a prosthetic socket cooling system employing such a heat pipe array and heat sink may also include an active device for reducing the temperature of the heat sink.

One example of an active device for cooling a heat sink is a fan. Another example of an active device for cooling a heat sink is a thermoelectric cooling device (e.g., a Peltier device). Of course, the heat sink may also include passive cooling elements such as cooling fins. Active cooling devices may also be used in combination in such embodiments. For example, a heat sink with cooling fins and a fan may be connected in parallel with a thermoelectric cooling device. Such an arrangement could allow cooling only via the heat sink and fan when conditions permit, with the thermoelectric cooling device being energized only when the cooling load exceeds the capacity of the heat sink and fan. A second heat sink and fan may be similarly connected in parallel to the thermoelectric cooling device and so on to provide sufficient cooling capacity. The active devices may be powered by one or more batteries or capacitors, or by another electrical energy storage device(s).

An alternative and wholly passive version of the hybrid prosthetic socket cooling system described above is also possible. For example, the active cooling device(s) of the aforementioned hybrid cooling system may be replaced with a phase change material that acts to transfer heat from the heat pipe array through the socket wall and to the atmosphere. In such an embodiment, the phase change material may be contained in a housing, container, etc., that is mounted to the exterior of a prosthetic socket. The housing would preferably be highly conductive along the surface thereof that communicates with the heat pipe array, but highly insulating along the surface(s) thereof that are exposed to the socket atmosphere. In this manner, it can be better ensured that the phase change material will always transfer heat from the heat pipes out of the socket, and will not inadvertently operate in reverse if conditions are encountered where the temperature outside of the socket exceeds the temperature within the socket.

In such an embodiment, a packet of a phase change material may again be employed so that, should the phase change material become heat saturated, replacement of the packet with another packet of phase change material in the solid phase is all that is required to restore full thermal regulation to the system. Similarly, the enclosure, etc., provided to retain the phase change material may again include a door(s) or some other convenient form of access to allow a user to readily exchange the phase change material if necessary.

In yet additional embodiments of the invention, other combinations of passive and active cooling may be used to enhance the heat transfer capabilities of a prosthetic socket. For example, a passive device other than a heat sink, or some combination of passive devices, could be used in conjunction with an alternative active device(s) such as a fan or a coolant circulating system, as described above.

With respect to the use of thermoelectric cooling devices in prosthetic socket and and/or orthotic device embodiments of the invention, it is noted that the coefficient of performance (COP) for a thermoelectric cooling system is generally understood to fall in the range of about 0.3 to 0.7, while typical evaporative cooling systems generally have a COP of around 3.0 (i.e., as much as ten times that of a thermoelectric cooling based system). It is apparent, therefore, that thermoelectric cooling systems are generally held to be highly inefficient.

In a prosthetics application, an amputee must generally carry a power supply for any electrical energy consuming devices associated with a prosthesis. A power supply adds weight and cost, and a convenient means of carrying such a power supply is also generally necessary. Consequently, it should be apparent that system efficiency is important in a prosthetic socket cooling application, and thermoelectric cooling devices have generally been thought to be far too inefficient for this purpose.

As explained above, efficiency in cooling applications is generally expressed as the COP. COP for a cooling application is defined as:

$$COP = \frac{Q_{Cold}}{Work} \quad (1)$$

Where $Q_{Cold}$ is the heat removed from the refrigerated system and Work is the energy necessary to drive the cooling. The heat exhausted from the system is therefore necessarily:

$$Q_{out} = Q_{cold} + Work \quad (2)$$

It is also important to note that there is an absolute limit to how high the COP can go. This limit is defined by Carnot's equation as:

$$COP_{max} = \frac{T_{cold}}{T_{hot} - T_{cold}} \quad (3)$$

A quick evaluation of Equation 3 reveals that operating a thermoelectric cooling device over a narrow temperature range can greatly increase the maximum COP that can be achieved. It is also important to note that COPs for thermoelectric cooling devices are generally much higher at comparatively low heat flux densities. Using these two factors, the fact that the amount of heat that needs to be removed from a prosthetic device (e.g., socket) is relatively low, and that the cost for a prosthetic device is relatively high compared to this amount of heat, it is possible to construct an efficient thermoelectric cooling system with a COP in the region of 3.0 by using a comparatively large thermoelectric cooling device for the amount of heat that needs to be pumped and capitalizing on the fact that a vast majority of an amputee's life is spent at temperatures below 40° C. Since typical socket temperatures of 30° C. are only 10° C. below this, the term $T_{hot}-T_{cold}$ in Equation 3 is unlikely to ever be above 10° C. This is a relatively low temperature differential compared to conventional thermoelectric cooling designs where temperature differentials of as high as 40° C.-50° C. are typically used to reduce device size and cost.

Research has shown that a residual limb produces a maximum heat load of only about 15 Watts. Thus, a thermoelectric cooling system need only meet this heat load to provide adequate socket cooling under normal circumstances. By increasing the COP of a thermoelectric device, the power requirements of the thermoelectric device may be further reduced (e.g., to 5 Watts with a COP of 3). As such, a thermoelectric cooling device of only a few square inches in size has sufficient power to cool a prosthetic socket. Further, and as discussed above, such a unit will seldom need to operate against more than 10° C. temperature differential. Therefore, it has been determined that if a thermoelectric cooling device is sized accordingly, and if a control scheme is designed to measure the current temperature differential and then choose the optimal drive power, it is possible to design an efficient thermoelectric cooling system for a prosthetic socket. While the cost per Watt of cooling utilized in a such a cooling application may be unacceptable in other applications, it is acceptable for use in a durable medical device such as a prosthetic socket.

One key to acceptable prosthetic socket cooling via a thermoelectric cooling device is proper (over)sizing of the cooling element so that at the highest anticipated temperature differential, the COP will still be acceptable. It is possible to operate a thermoelectric cooling device at the peak COP by controlling either the drive voltage or the drive current. Because the system is constrained, controlling one will result in operation at the proper operating point of the other.

For a thermoelectric cooling device made of P type and N type semiconductor materials at specific temperatures, Goldsmid teaches that the maximum COP will be obtained by running the device at a specific current that can be calculated by using Equation 4 below.

$$I_{COPmax} = \frac{(\alpha_p - \alpha_n)(T_2 - T_1)}{(R_p + R_n)\left((1 + ZT_m)^{\frac{1}{2}} - 1\right)} \quad (4)$$

Where $\alpha_p$ and $\alpha_n$ are the Seebeck coefficients for the P and N doped legs of the thermoelectric cooling device; $T_s$ and $T_1$ are the temperatures of the two sides of the thermoelectric cooling device; $R_p$ and $R_n$ are the electrical resistances of the P and N doped legs of the thermoelectric cooling device; Z is the figure of merit for a given combination of materials; and $T_m$ is the average of $T_2$ and $T_1$.

It is further known that the voltage in a thermoelectric cooling device is related to current by Equation 5 below:

$$V = I \times R_{tec} + \alpha(T_2 - T_1) \quad (5)$$

Therefore, Equation (4) and the voltage Equation (5) can be used to control a thermoelectric cooling device by either current or voltage control systems. Key points of consideration are to select a thermoelectric cooling device of a size that is capable of pumping a sufficient amount of heat from the prosthetic socket at a high COP and, preferably, operating the thermoelectric cooling device only at the optimal COP. Attempts to provide proportional control should be implemented by switching the thermoelectric cooling device on and off such that the level of cooling is controlled by the duty cycle.

Figure 19:
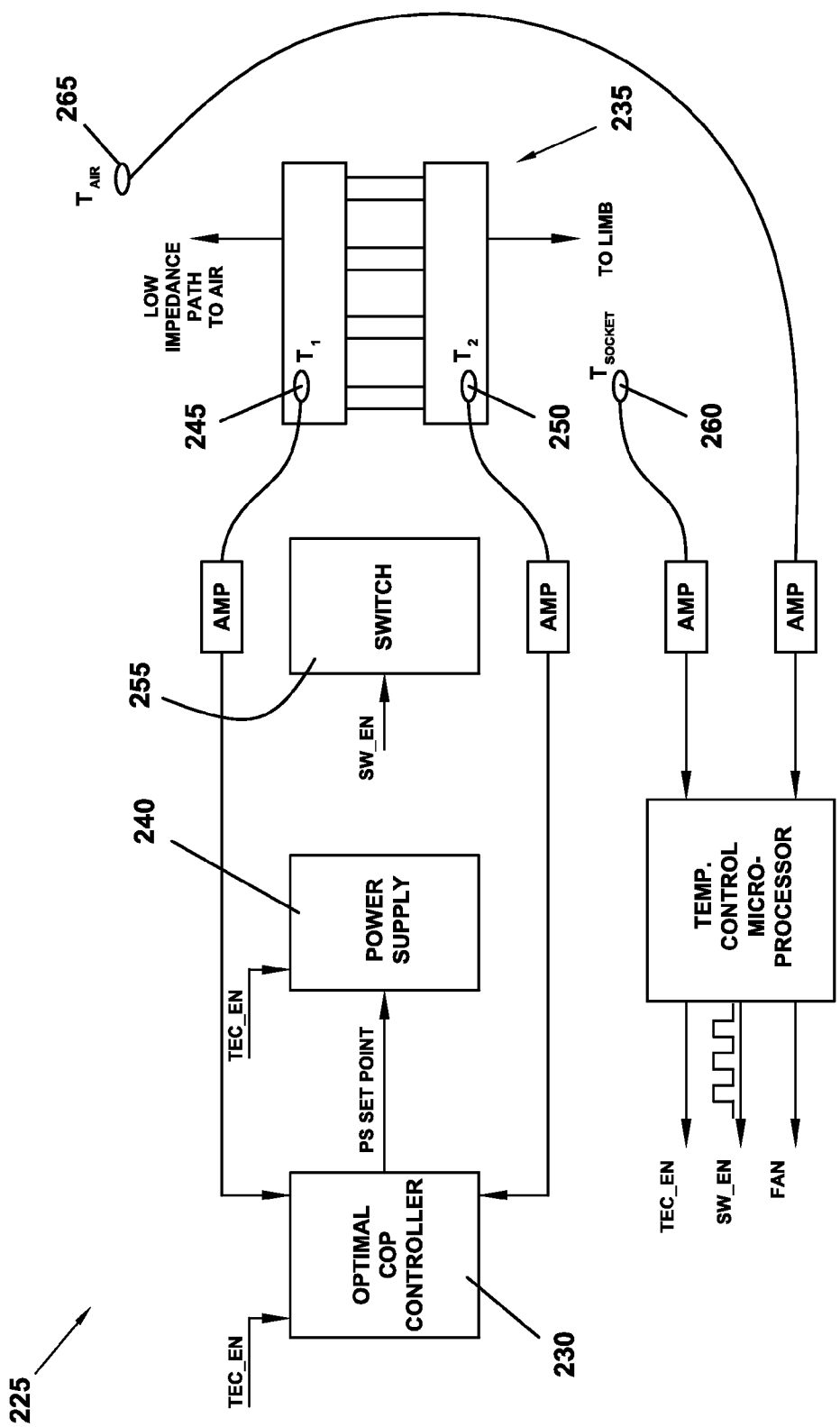
FIG. 19 schematically represents one exemplary control methodology for controlling a thermoelectric cooling device/system for the purpose of cooling a prosthetic socket.

As explained above, known systems have failed to realize that efficient thermoelectric cooling can be achieved if the thermoelectric cooling device is massively oversized and appropriately controlled. Therefore, in embodiments of the invention where a thermoelectric cooling device is employed, it is possible to design and control a thermoelectric cooling system in a manner that results in a much higher than normal coefficient of performance (COP) while still providing adequate cooling of the prosthetic socket. FIG. 19 schematically represents one exemplary control system 225 and associated methodology for operating a thermoelectric cooling device in such a manner.

The exemplary system design of FIG. 19 includes two control loops. The first control loop is comprised of an optimal COP controller 230, a thermoelectric cooling device 235, a thermoelectric cooling device power supply 240, and thermocouples 245, 250 in communication with both sides of the thermoelectric cooling device.

The first control loop uses temperature feedback from the thermoelectric cooling device 235 and Equation 1 above to determine the optimal power setting for the thermoelectric cooling device and to adjust the power supply 240 accordingly. This power setting is then applied to the input of a switch 255 so that any time the switch is enabled, the thermoelectric cooling device 235 will immediately start to operate at its most efficient setting.

The second control loop is comprised of the thermoelectric cooling device 235, a thermocouple 260 that provides a temperature reading from inside the prosthetic socket, a thermocouple 265 that provides the temperature of the ambient air, and the power switch 255, which is connected to the thermoelectric cooling device 235. This second control loop enables the switch 255 when it is necessary to transfer heat away from (remove heat from) the inside of the prosthetic socket.

It is important to recognize that the switch 255 as used herein is truly on or off, and that when partial power is necessary, the switch will function in a Pulse Width Modulation (PWM) mode so that the thermoelectric cooling device 235 is either off, or operating at optimal efficiency. The switch 255 can be a simple switch when only cooling will be provided. Alternatively, the switch 255 may be a directional H-Bridge type switch when both cooling and heating of the prosthetic socket will be practiced.

With these two control loops working in concert, the thermoelectric cooling device 235 will only be turned on when there is a need to remove heat from or deliver heat to the prosthetic socket, and the thermoelectric cooling device will never be at any operating point other than its most efficient operating point.

As noted in FIG. 19, maintaining a low impedance heat path to the environment is important. However, it is realized that prosthetic sockets are typically custom built devices and each socket could have widely varying characteristics. As such, it is not possible to predict the amount of heat driven by such a system without evaluating the specific patient who will use a given prosthetic socket. Consequently, the actual design of this heat path can vary widely. For low activity patients with smaller sockets, a simple heat sink might suffice. Larger and more active patients might require that more heat be rejected and, thus, a larger heat sink or perhaps even a fan-cooled heat sink may be needed. For this reason, a control output is shown from the temperature control module. This control could also be derived from outputs from the COP controller, power supply, or a combination of these sources.

Figure 20:
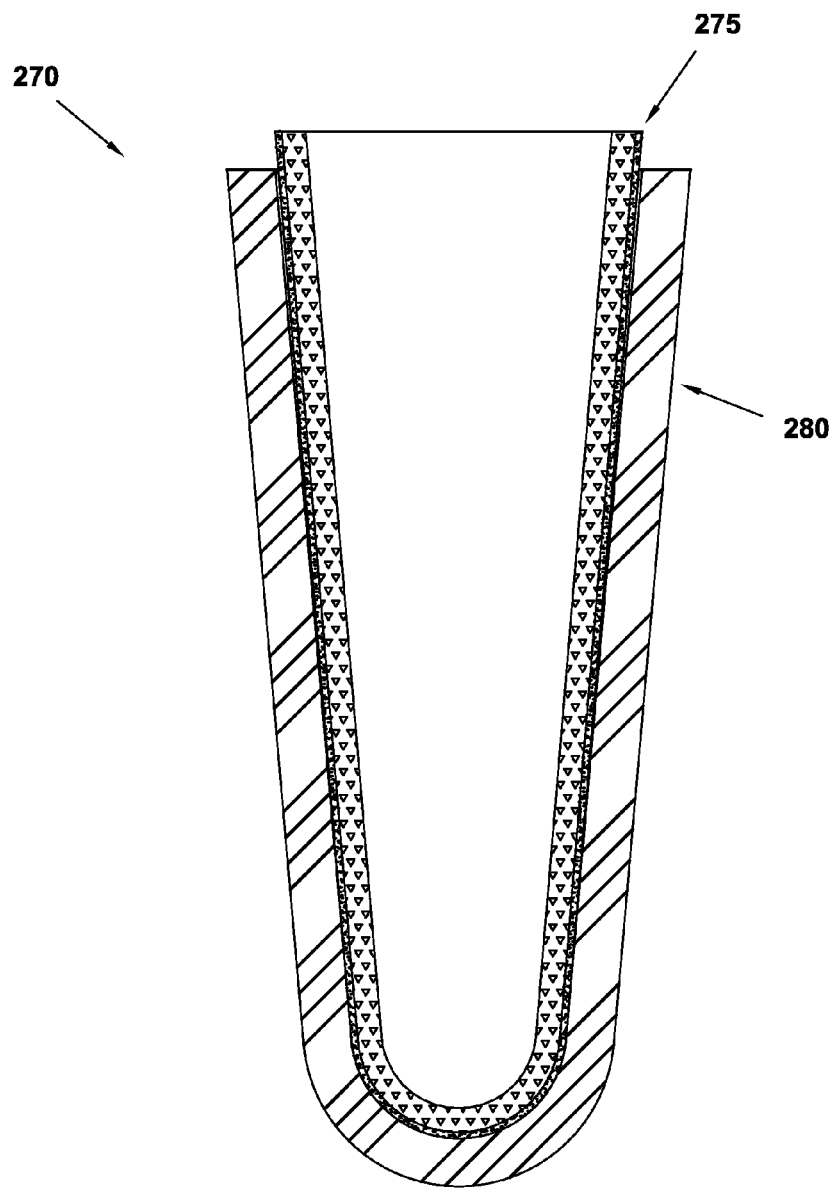
FIG. 20 is a cross-sectional view of one exemplary embodiment of a prosthetic assembly of the invention.

One exemplary assembly 270 of a prosthetic liner 275 and a prosthetic socket 280, both having enhanced thermal conductivity, is shown in FIG. 20. In this exemplary embodiment, the liner 275 is shown to have a similar construction to the exemplary liner embodiment of FIG. 2, but any of the other prosthetic liner embodiments described herein, or combinations of those embodiments, are also possible. Similarly, the prosthetic socket 280 is shown to have a similar construction to the exemplary prosthetic socket embodiment of FIG. 13, but any of the other prosthetic socket embodiments described herein, or combinations of those embodiments, are also possible. In practice, the liner 275 would be donned over a residual limb (not shown) prior to insertion into the prosthetic socket 280.

Prosthetic assemblies of the invention may include combinations of any liner and any prosthetic socket that falls within the scope of the invention, including embodiments that also exhibit enhanced heat absorption capabilities. Additionally, prosthetic assemblies of the invention may include the use of said liners and prosthetic sockets in combination with passive cooling devices, active cooling devices, or combinations thereof. Therefore, while one exemplary embodiment of a prosthetic assembly is depicted in FIG. 20 for purposes of illustration, prosthetic assemblies of the invention are in no way limited to the illustrated combination. Rather, any embodiment of a liner of the invention may be used with any embodiment of a socket of the invention to improve the transfer of heat away from and/or the absorption of heat produced by a residual limb.

Figure 21:
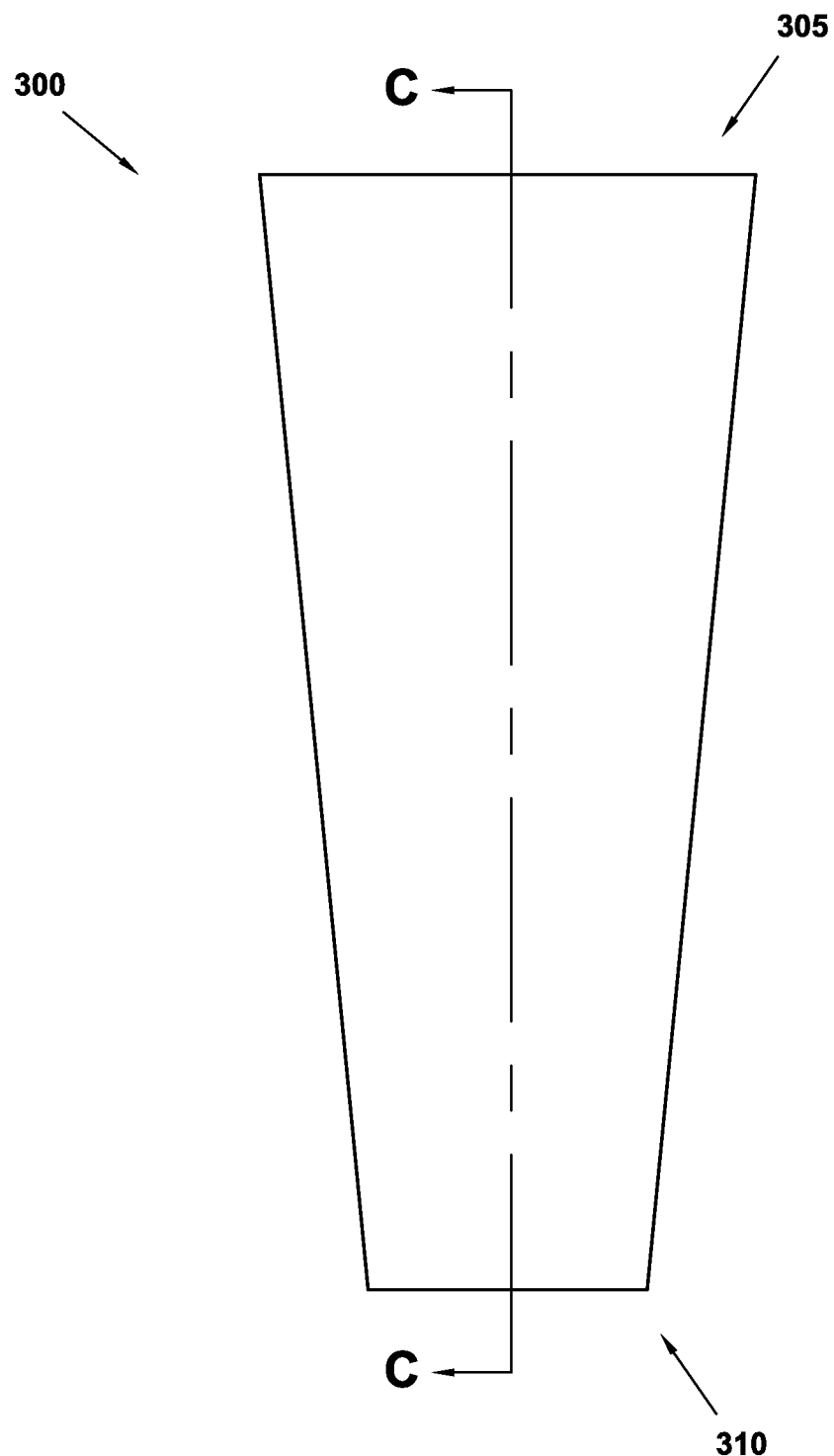
FIG. 21 represents an exemplary embodiment of a prosthetic suspension sleeve of the invention.

A prosthetic suspension sleeve 300 having enhanced thermal conductivity (heat transfer capabilities) according to the invention is generically depicted in FIG. 21. As shown, the suspension sleeve 300 is substantially tubular in nature and includes two open ends 305, 310.

As used herein, the term "tubular" is intended to denote only that a suspension sleeve is a continuous hollow structure of some length. As would be understood by one of skill in the art, a suspension sleeve according to the invention may have a generally circular cross section when in use, although the flexible nature thereof also permits the suspension sleeve to conform to other cross-sectional shapes. Suspension sleeves according to the invention may have a taper, as shown. When present, the degree of taper may vary. Other suspension sleeve embodiments may be substantially cylindrical (i.e., may have a substantially uniform cross-sectional diameter along the entire length). Yet other embodiments may have a larger cross-sectional diameter at or near a mid-point than at each end. These designs and others would be well known to one of skill in the art, and all are considered to be "tubular," as well as falling within the scope of the invention.

Figure 22:
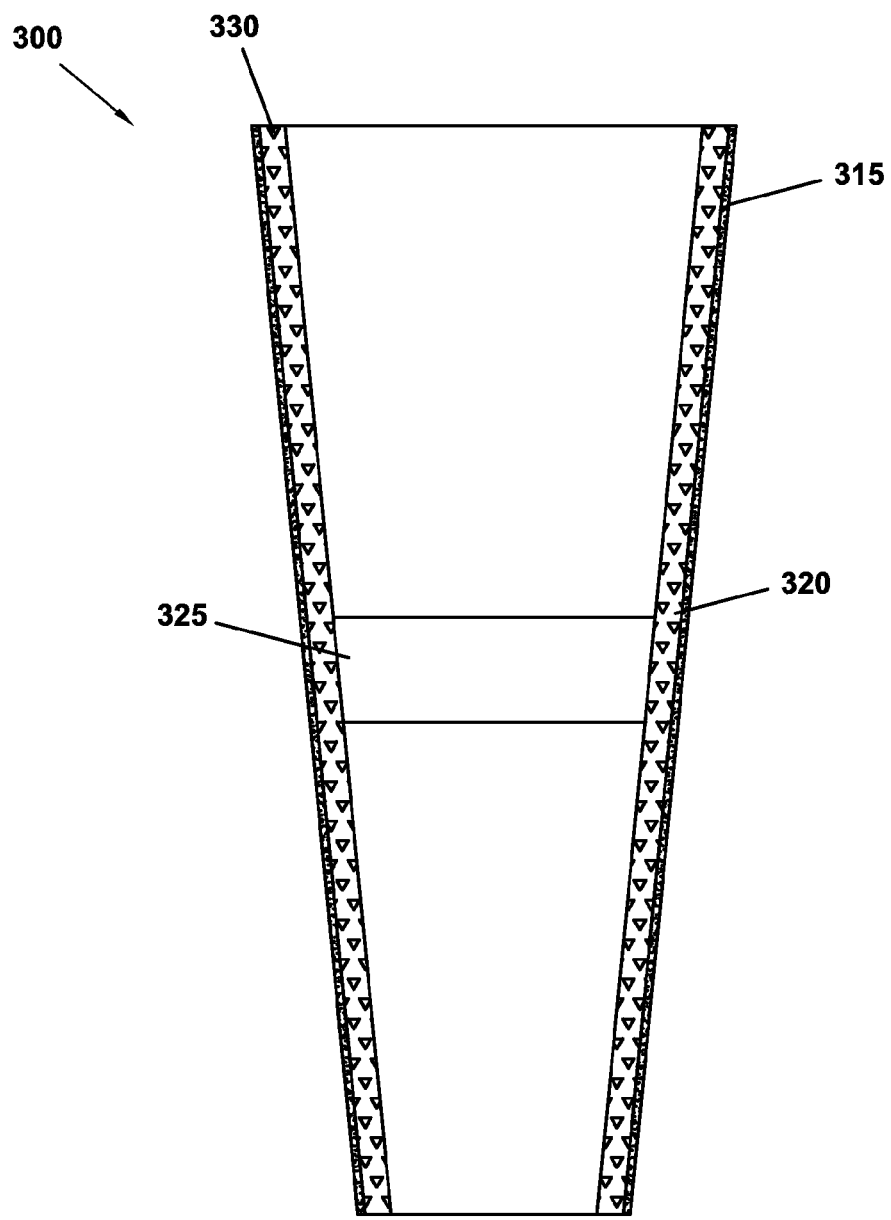
FIG. 22 is a cross-sectional view of an exemplary embodiment of a prosthetic suspension sleeve of the invention.

A cross-sectional view of the suspension sleeve 300 of FIG. 21 can be observed in FIG. 22. As shown, the suspension sleeve 300 includes a fabric material 315 that covers the exterior of the suspension sleeve when the suspension sleeve is in a normal (i.e., right side out) orientation. The fabric material 315 may be wholly or partially absent from the exterior of the suspension sleeve in other embodiments.

A flexible polymeric material 320 resides on an interior surface of the fabric material. A portion of the polymeric material 320 at one end 305 of the suspension sleeve will overlap an amputee's residual limb when the suspension sleeve 300 is in use. This portion of the polymeric material 320 may be in contact with the skin of the amputee's residual limb and/or a prosthetic liner covering the residual limb. Another portion of the polymeric material 320 at the opposite end 310 of the suspension sleeve 300 will overlap and be in contact with the exterior of a prosthetic socket when the suspension sleeve 300 is in use.

The suspension sleeve 300 may also include an optional circumferential band 325 along its interior. The interior band 325 may be formed of a fabric material, which may be the same as or dissimilar to the fabric material 315 that covers all or a portion of the exterior of the suspension sleeve 300. The band 325 may allow for easier manipulation of the suspension sleeve 300 over a residual limb and prosthetic socket, and may also produce an area of reinforcement. The band 325 may be located at various points along the length of the suspension sleeve 300, but is preferably located at or near the point where the suspension sleeve will overlap the brim of a prosthetic socket when in use. When present on a suspension sleeve of the present invention, a band may fully circumvolve the interior of the sleeve, or may cover only a section of the sleeve interior.

The polymeric material portion of a suspension sleeve of the invention may be comprised of any of the materials mentioned above with respect to prosthetic liners of the invention. The polymeric material of a suspension sleeve according to the invention may also be treated to enhance the thermal conductivity thereof, as previously described.

As shown in FIG. 22, the heat transfer capability of the polymeric material 320 of the suspension sleeve 300 has been enhanced by the inclusion therein of additives/fillers 330. The additives/fillers 330 are dispersed throughout the polymeric material 320 in this exemplary embodiment. Suitable additives/fillers 330 may include, without limitation, any of the additives/fillers disclosed or referred to above in regard to prosthetic liners of the invention.

The fabric portion of a suspension sleeve of the invention may be comprised of any fabric material mentioned above with respect to a prosthetic liner of the invention. The fabric used in a suspension sleeve of the invention may inherently exhibit good thermal conductivity. Alternatively, and as explained above in regard to prosthetic liners of the invention, the fabric of a suspension sleeve may be modified to produce or enhance the thermal conductivity thereof.

As with prosthetic liner embodiments of the invention, suspension sleeve embodiments may also be highly heat absorbing instead of, or in addition to, possessing enhanced heat transfer capabilities. Generally, the heat absorbing capability of a suspension sleeve of the invention, like a liner of the invention, is enhanced through the use of a phase change material.

Figure 23:
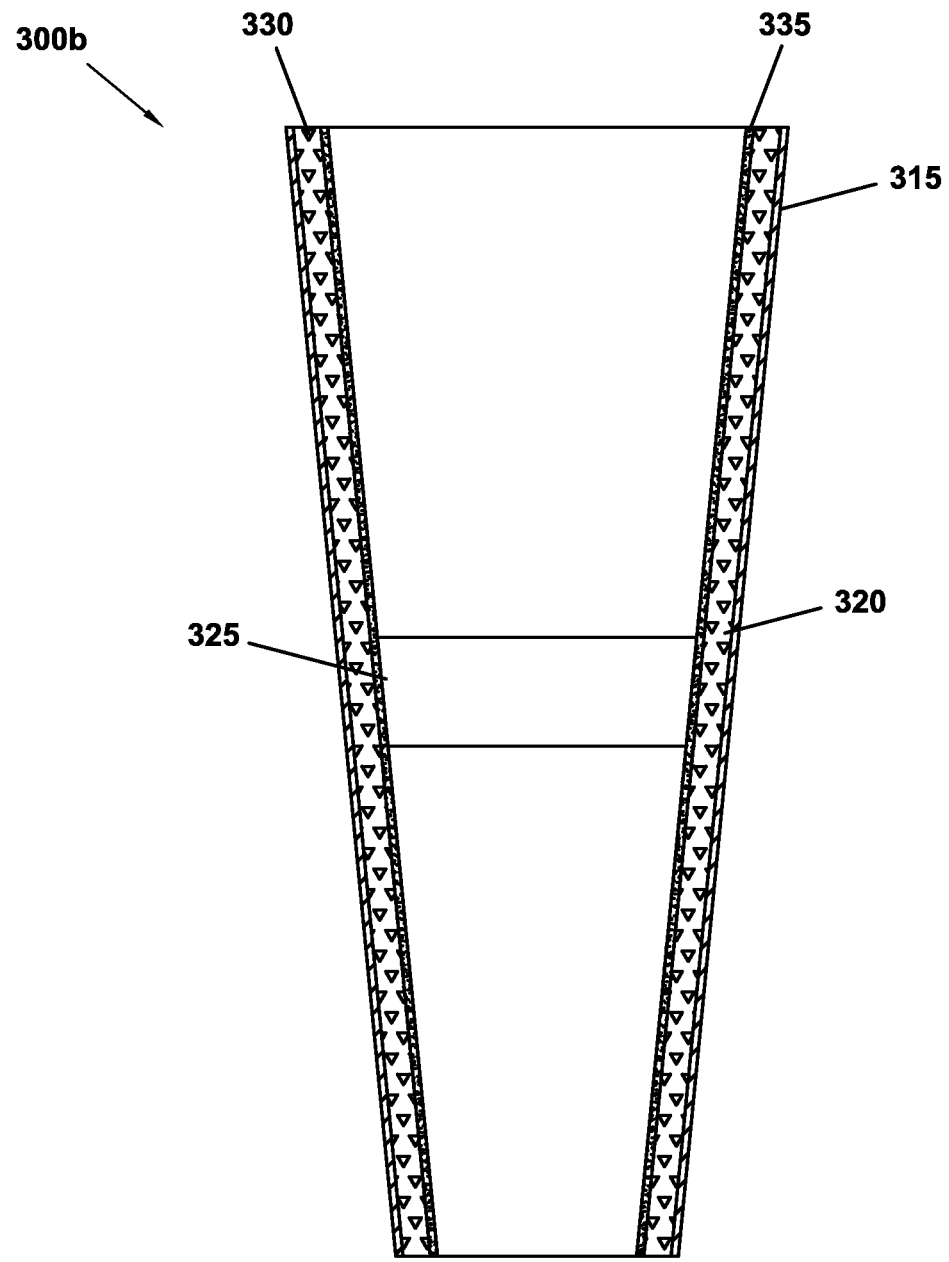
FIG. 23 is a cross-sectional view of another exemplary embodiment of a prosthetic suspension sleeve of the invention.

An alternate embodiment of a suspension sleeve 300b having both enhanced thermal conductivity and heat absorption capabilities is shown in FIG. 23. This exemplary embodiment of the suspension sleeve 300b is again comprised of a polymeric material 320 having a fabric outer covering 315. The heat transfer capability of the polymeric material 320 of the suspension sleeve 300b has also again been enhanced by the inclusion therein of additives/fillers 330 that are dispersed throughout the polymeric material.

Unlike the exemplary suspension sleeve 300 embodiment of FIG. 22, this exemplary suspension sleeve 300b also includes a phase change material 335 that is provided in a layer of some thickness over all or part of the suspension sleeve 300b. Preferably, and as shown, the phase change material 335 is located along an area of the suspension sleeve 300b that will reside near the skin of an amputee's residual limb and a prosthetic socket when the suspension is worn, so as to most effectively absorb heat from the residual limb and socket and transfer the heat to the ambient environment. The fabric 315 of the suspension sleeve 300b may also have good inherent thermal conductivity or may be enhanced as previously described.

Figure 24:
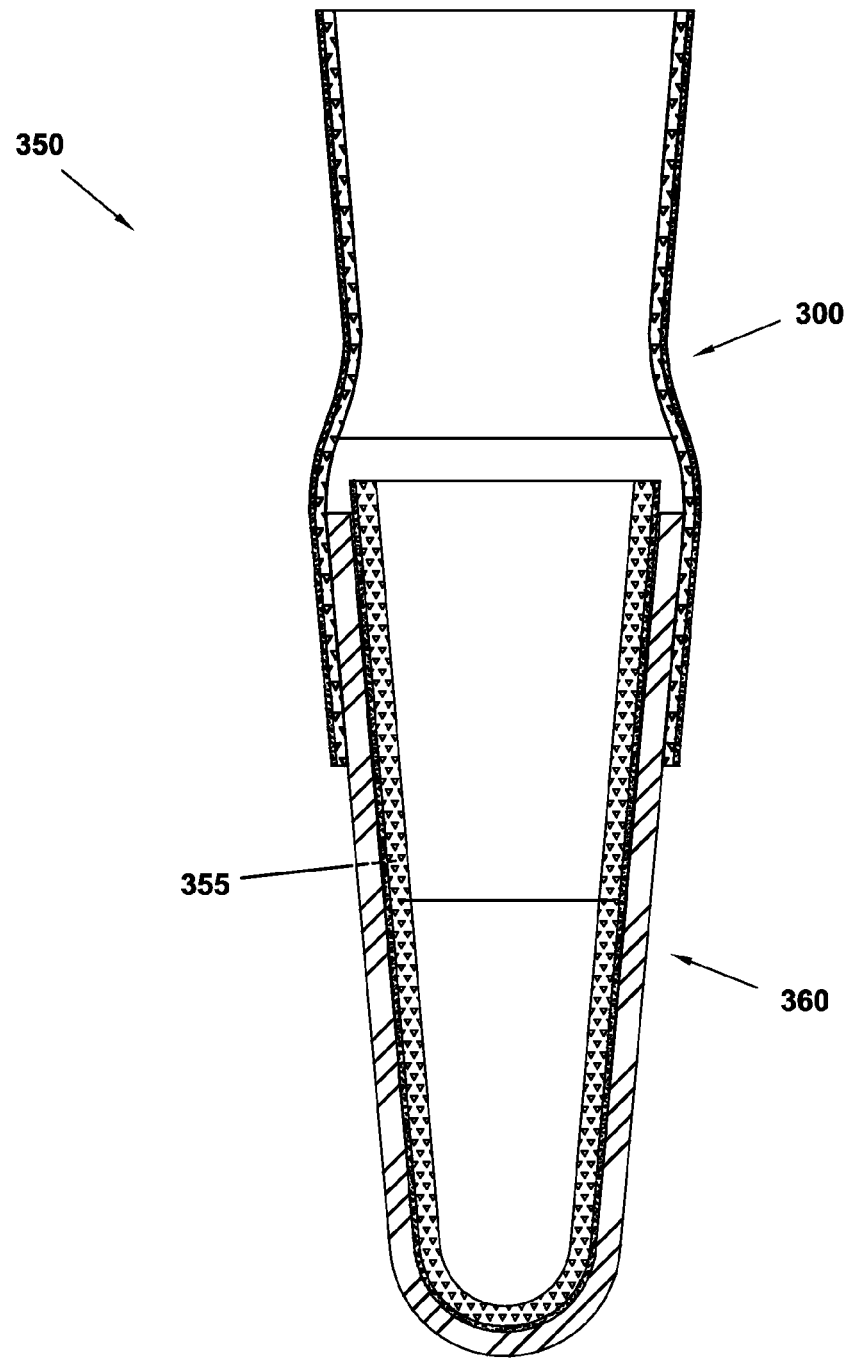
FIG. 24 is a cross-sectional view of another exemplary embodiment of a prosthetic assembly of the invention.

Another exemplary assembly 350 of a prosthetic liner 355 and a prosthetic socket 360, both having enhanced thermal conductivity, is shown in FIG. 24. This exemplary prosthetic assembly embodiment is very similar to the exemplary prosthetic assembly shown in FIG. 20, except this exemplary assembly 350 also includes the suspension sleeve 300 of FIG. 22. In a like manner to the prosthetic assembly 270 shown in FIG. 20, a prosthetic assembly such as that shown in FIG. 24 may utilize any prosthetic liner, prosthetic socket and prosthetic suspension sleeve according to the invention, and in any combination. It is also possible for prosthetic assemblies of the invention to mix components having enhanced thermal conductivity and/or heat absorption capabilities with traditional components. For example, while it may not be ideal, a prosthetic liner with enhanced heat absorption capabilities may be worn with a standard (non-enhanced) prosthetic socket and suspension sleeve.

Referring again to the subject of prosthetic hard sockets, research has shown that one of the primary challenges in maintaining a comfortable socket temperature is overcoming the limitations of convective cooling at the exterior surface of the socket. Convective cooling is more effective with higher temperature differentials between the air and the surface to be cooled. Unfortunately, a high temperature differential means a low external temperature that will be carried through to the amputee. Furthermore, convective cooling can never cool a surface below the ambient temperature, which necessarily limits the performance of systems that use convective cooling to environments with relatively cool temperatures.

The aforementioned issues make the use of phase change materials in a prosthetic liner and socket particularly attractive, as the use of a phase change material may allow convective cooling to be avoided altogether. Relatively simple and effective systems can be made by completely bypassing convective cooling and relying entirely on phase change materials.

One useful and simple embodiment of such a device is a thermally conductive prosthetic (hard) socket with an inner wall, an outer wall, and region of phase change material interposed therebetween. Such an exemplary embodiment is shown in cross-section in FIG. 25. In this embodiment, the socket 400 is a double wall socket having an inner wall 405 and an outer wall 410. The inner wall 405 and outer wall 410 are shown to be in contact and joined in a sealed manner for some distance along an open proximal end 415 and a closed distal end 420 of each wall and the resulting socket. The joined distance of the inner wall 415 and outer wall 410 may vary between embodiments.

Between the proximal end 415 and distal end 420 of the socket 400, the inner wall 405 and outer wall 410 are separated by a space of some length and some height, both of which may vary between embodiments. The space is filled or substantially filled with a phase change material 425.

Each of the inner wall 405 and outer wall 410 could be of a laminate or thermoplastic material. Each could also be either traditional socket materials, or those with improved thermal properties. Preferably, at least the inner wall 405 of the socket 400 is comprised of a high thermal conductivity material so as to facilitate heat flow from, or to, the residual limb of the user.

The choice of material for the outer wall 410 of the socket 400 might depend on the typical environment to which the associated user is exposed. For example, for those users typically exposed to temperatures below the melting point of the phase change material 425, but above uncomfortably cold temperatures, it would likely be beneficial for the outer wall 410 to also have improved thermal conductivity properties. For users that are typically exposed to temperatures that are higher or lower than a normal comfort range, an insulated outer surface may be desirable.

Such a socket is simple to construct, provides significant thermal buffering, and is relatively inexpensive. When such a socket is used to buffer against heat, the phase change material within the socket may be recharged simply by setting the socket in a cool area for some period of time. When such a socket is used to buffer against cold, the phase change material within the socket may be recharged simply by setting the socket in a heated area for some period of time. A simple device designed to blow either cool or warm air at the area of the socket containing the phase change material could also be used to facilitate recharging. A blower device or another heat transfer device capable of effecting a temperature change may be equipped with cold and hot settings and provided as a useful accessory to a socket system for this purpose.

As can be appreciated by one of skill in the art, it would be desirable if a phase change material for inclusion in such a socket has not only a high latent heat density, but also a high thermal conductivity. It would also be useful, although not essential, if the phase change material is not of a type where a phase change might result in a phase where the material loses shape constraint, i.e., a liquid or gas phase. To this end, a high thermal conductivity phase change material in the form of a gel may be particularly useful for a prosthetic socket application. Such a phase change gel material may be created, for example, by combining a phase change material, a thermal conductivity enhancing component, and a gelling component. The resulting phase change gel material will be able to hold its shape when the phase change material is in a melted phase.

There are many known phase change materials. Testing has revealed that octadecane and eicosane perform particularly well in this application, but such a socket embodiment is not limited to use of only these two materials. Gelling agents used in a phase change gel material embodiment may include a wide range of materials. For example, block copolymers such as SEBS (e.g., Kraton G1651 ES) have been found to perform particularly well in this role. The range of thermal conductivity additives is also very broad. Large aspect ratio graphenes such as 15 and 25 micron, Grade M, xGnP® Nanoplatelets from XG Sciences have proven very effective as thermal conductivity additives during testing. Appropriately compounded mixtures of these materials have resulted in gels with latent heats of approximately 80% of that of a pure phase change material, thermal conductivities of over three times the thermal conductivity of the phase change material used, and very favorable mechanical properties for use in the fabrication of prosthetic sockets.

The resulting gel is firm when cooled, and becomes softer and more elastic when heated. Functional elongations of such materials have exceeded 200% in testing. In the heated state, the phase change gel material is easily shaped. Fabrication may also be facilitated by molding such a phase change gel material into a pre-defined shape. Many useful shapes are possible, including but not limited to, strips, tubes, circles, and ovals that can be wrapped around the inner wall of the socket. Shapes with a wall thickness of approximately 6 mm appear to strike a reasonable balance between bulk and thermal buffering capacity, although other wall thicknesses are also possible to permit greater socket customization. When using such a technique, a practitioner (e.g., prosthetist) is able to easily scale the amount of phase change material to an individual user. For example, highly active users might be provided with a socket having several layers of a phase change material, while a less active patient might be provided with a socket having only a single layer.

As would be recognized by one of skill in the art, a socket having a phase change material trapped between an inner and outer wall must have sufficient space therebetween to allow for expansion and contraction of the phase change material when it changes phase. There are a number of ways to provide for such space. For example, the outer wall of such a socket may be formed over the phase change material when the phase change material is in the state where it occupies the largest volume (e.g., the melted phase in the case of a phase change gel material). Alternatively, a layer of a compressible material may be placed over the phase change material prior to forming the outer wall of the socket, such that the volume of the compressible material may be later compressed upon expansion of the phase change material. It is also possible to mix air into a phase change material or a phase change gel material in a ratio that creates a low air, foam-type, material that provides for sufficient expansion space within the material. Other socket forming and/or other molding techniques known in the art may also be used.

With respect to the use of graphene as a thermally conductive additive, research has shown that a high electric field can be used to orient graphene particles and, in so doing, greatly improve the thermal conductivity of the resulting material in one direction. Use of this technique when graphene is added to the material of a socket (or to a liner or phase change gel material) may considerably reduce the amount of graphene necessary to achieve acceptable thermal conductivities, and significantly reduce the associated effects of graphene on the mechanical properties of these materials.

Figure 25:
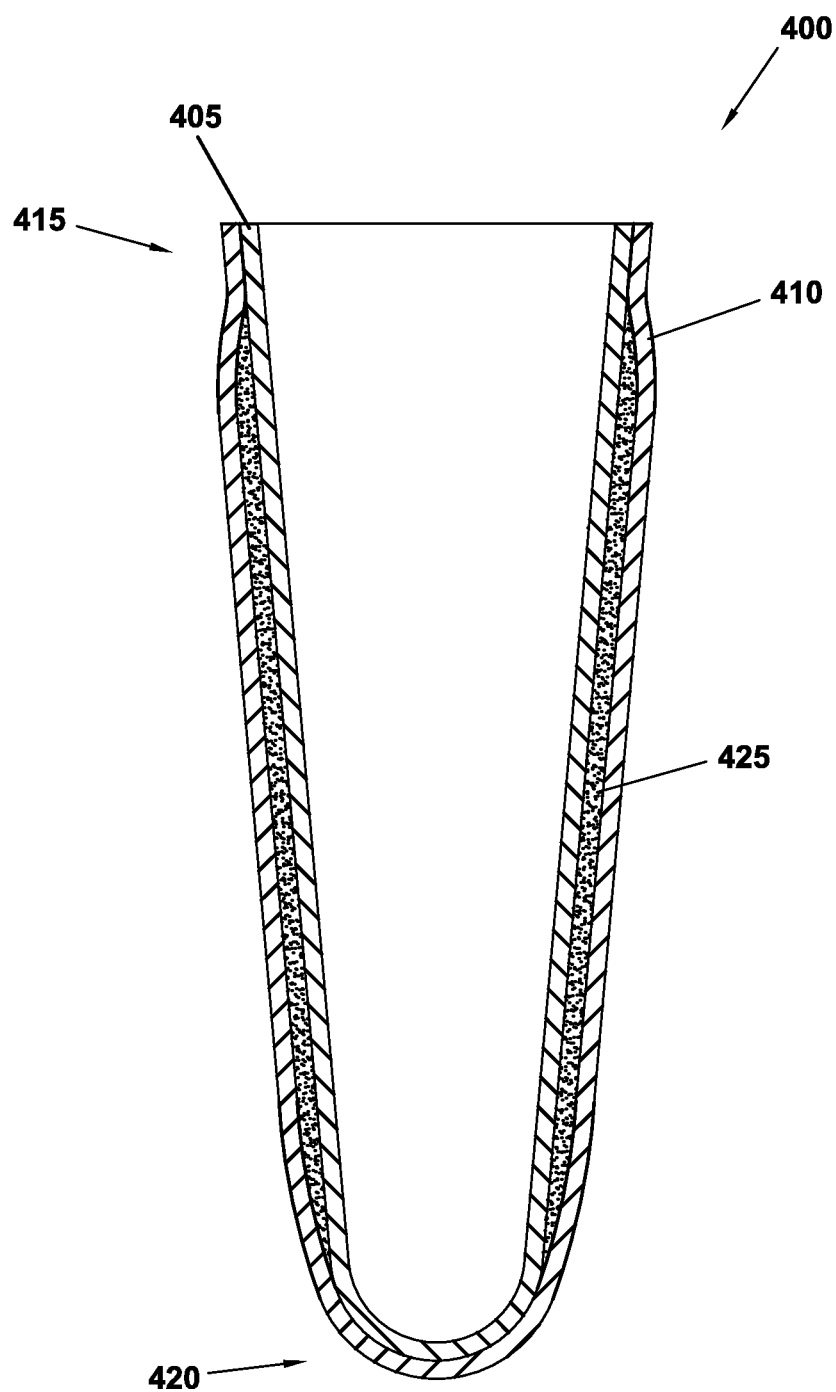
FIG. 25 is a cross-sectional view of another exemplary embodiment of a prosthetic hard socket of the invention.

A thermally conductive prosthetic socket 400 such as that shown in FIG. 25 and described above may also include other thermally conductive materials or devices, such as any of the materials and devices mentioned above. To this end, one or both of the socket walls of the exemplary socket 400 may be made from an inherently conductive material and/or may be made from a material whose conductivity is enhanced. Similarly, active or passing cooling devices may be used in conjunction with the socket 400.

Figure 26:
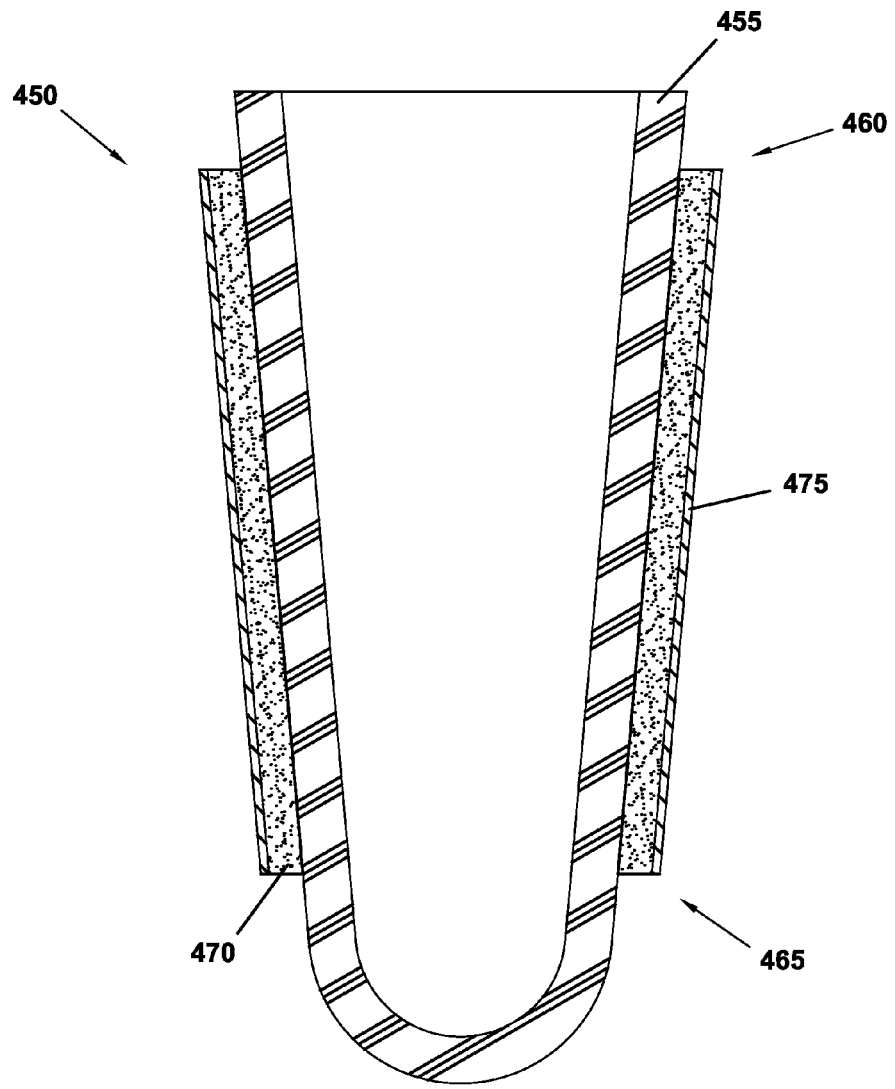
FIG. 26 is a cross-sectional view of an exemplary embodiment of a cooling sleeve of the invention.

A section-view of an exemplary embodiment of a cooling sleeve 450 according to the invention is shown in place around a prosthetic socket 455 in FIG. 26. In similar fashion to the previously described exemplary suspension sleeves, the cooling sleeve 450 is also substantially tubular in nature and includes two open ends 460, 465. The term "tubular" as used with respect to a cooling sleeve is intended to have the same meaning as described previously with respect to a suspension sleeve. A cooling sleeve may also be tapered or non-tapered in shape, and/or may conform to various socket shapes.

The cooling sleeve 450 may be used to avoid the socket cooling limitations imposed by convective cooling by adding latent heat to the socket system. The cooling sleeve 450 may have very high latent heat capacity, and be removable (for recharging or replacement purposes).

In the exemplary embodiment shown in FIG. 26, the cooling sleeve 450 is comprised of a phase change material 470 whose exterior surface is covered with a layer of fabric 475 for purposes such as protecting the phase change material from damage, preventing overlying clothing from sticking to the phase change material, etc. A similar layer of fabric may also or instead reside along the interior surface of the phase change material. When present, the fabric may be an inherently thermally conductive fabric or the fabric may be treated to enhance thermal conductivity, as previously described.

Materials other than fabric may also be applied to the phase change material, such as a durable polymer coating, or an exterior insulating layer (e.g., foam) for use in hot conditions so that the phase change material does not try to cool the environment as well. Alternatively, appropriate formulation of a polymer phase change material may allow for direct application of a cooling sleeve to a socket, without the use of a fabric or other protective material.

The use of a cooling sleeve, such as the exemplary cooling sleeve 450 shown in FIG. 26, has been shown in testing to effectively reduce the ambient temperature to approximately 80° F. Such a cooling sleeve may also eliminate the temperature rise associated with the convective cooling interface of the air and the surface of a socket to which it is applied. For an active AK amputee, for example, this might be as much as an additional 6° F.

It is to be understood that the exemplary embodiments of prosthetic and orthotic devices described and shown herein are provided only for purposes of illustration, and are not to be taken as limiting the scope of the invention only to the design, construction and/or arrangement of said exemplary embodiments. Rather, prosthetic and orthotic device, assembly and system embodiments according to the invention may include a multitude of various combinations of the features described and shown herein. For example, a prosthetic liner according to the invention may employ a polymeric material that exhibits both enhanced heat transfer and enhanced heat absorption capabilities—such as by dispersing both a thermally conductive additive/filler and a phase change material throughout the polymeric material. The exterior of such a liner embodiment may be wholly or partially covered by fabric, or may be completely devoid of any fabric covering. The fabric covering, if present, may or may not be imparted with enhanced heat transfer capabilities. Such a liner embodiment may also include one or more areas of localized phase change materials, such as in any of the embodiments represented in FIGS. 9-11.

Such a liner with enhanced heat transfer and heat absorption capabilities may be used in conjunction with a prosthetic socket and/or suspension sleeve of the invention. Again, a multitude of combinations are possible such that one to all of a prosthetic liner, prosthetic socket and prosthetic suspension sleeve of a given prosthetic assembly/system may have enhanced heat transfer and advanced heat absorption capabilities. Further, and as should be apparent, more than one heat transfer or heat absorption enhancing technique may be applied to a given prosthetic liner, prosthetic socket or prosthetic suspension sleeve according to the invention.

Therefore, while various exemplary embodiments of prosthetic liners, prosthetic sockets and prosthetic suspension sleeves having enhanced thermal conductivity (heat transfer) and/or heat absorption capabilities have been shown and described herein for purposes of illustration, the scope of the invention is not to be considered limited by such disclosure, and modifications are possible without departing from the spirit of the invention as evidenced by the following claims:

What is claimed is:

1. A thermally conductive prosthetic socket configured to fit over at least a portion of a residual limb having a distal end, comprising:
    a hard inner wall configured to reach circumferentially around the residual limb, the inner wall having a proximal end that is open for insertion of the residual limb and a distal end configured to reach radially across the distal end of the residual limb;
    an outer wall surrounding the inner wall across an internal space that reaches circumferentially entirely around the inner wall radially between the inner wall and the outer wall; and
    a phase change material residing in the internal space and reaching circumferentially entirely around the internal space;
    wherein the outer wall is sealed to the inner wall to define a double wall structure enclosing and isolating the internal space and the phase change material from an exterior of the double wall structure; and
    wherein one or both of the inner wall and outer wall of the socket are comprised of a material selected from the group consisting of a resin doped with at least one conductive additive and an inherently thermally conductive resin formed by an additive manufacturing technique.

2. A thermally conductive prosthetic socket configured to fit over at least a portion of a residual limb having a distal end, comprising:
    a hard inner wall configured to reach circumferentially around the residual limb, the inner wall having a proximal end that is open for insertion of the residual limb and a distal end configured to reach radially across the distal end of the residual limb;
    an outer wall surrounding the inner wall across an internal space that reaches circumferentially entirely around the inner wall radially between the inner wall and the outer wall; and
    a phase change material residing in the internal space and reaching circumferentially entirely around the internal space;
    wherein the outer wall is sealed to the inner wall to define a double wall structure enclosing and isolating the internal space and the phase change material from an exterior of the double wall structure; and
    wherein the phase change material is a phase change gel material comprising a mixture of a phase change material, a thermal conductively enhancing component, and a gelling component.

3. The thermally conductive prosthetic socket of claim 2, wherein the gelling component is a block copolymer.

4. The thermally conductive prosthetic socket of claim 2, wherein the thermal conductively enhancing component is large aspect ratio graphene particles.

5. The thermally conductive prosthetic socket of claim 4, wherein the graphene particles are aligned.

6. A thermally conductive prosthetic socket configured to fit over at least a portion of a residual limb having a distal end, comprising:
    an inner wall configured to reach circumferentially entirely around the residual limb, the inner wall having a proximal end that is open for insertion of the residual limb and a distal end configured to reach radially across the distal end of the residual limb;

an outer wall surrounding the inner wall across an internal space that reaches circumferentially entirely around the inner wall radially between the inner wall and the outer wall; and a phase change material residing in the internal space and reaching circumferentially entirely around the internal space;

wherein the outer wall is sealed to the inner wall to define a double wall structure enclosing and isolating the internal space and the phase change material from an exterior of the double wall structure; and wherein the inner wall and the outer wall are joined and sealed directly together across the distal end of the inner wall.

7. A thermally conductive prosthetic socket configured to fit over at least a portion of a residual limb having a distal end, comprising:

an inner wall configured to reach circumferentially entirely around the residual limb, the inner wall having a proximal end that is open for insertion of the residual limb and a distal end configured to reach radially across the distal end of the residual limb;

an outer wall surrounding the inner wall across an internal space that reaches circumferentially entirely around the inner wall radially between the inner wall and the outer wall; and a phase change material residing in the internal space and reaching circumferentially entirely around the internal space;

wherein the outer wall is sealed to the inner wall to define a double wall structure enclosing and isolating the internal space and the phase change material from an exterior of the double wall structure; and wherein the inner wall and the outer wall are joined and sealed directly together circumferentially entirely around the inner wall at proximal and distal ends of the inner wall.

8. A thermally conductive prosthetic socket configured to fit over at least a portion of a residual limb having a distal end, comprising:

an inner wall configured to reach circumferentially entirely around the residual limb, the inner wall having an open end for insertion of the residual limb and a closed end configured to reach radially across the distal end of the residual limb;

an outer wall having an open end joined in a sealed manner to the open end of the inner wall circumferentially around the open end of the inner wall, and having a closed end joined in a sealed manner to the closed end of the inner wall radially across the closed end of the inner wall, such that a sealed space is formed to reach between the inner wall and the outer wall longitudinally entirely between the joined ends thereof and circumferentially entirely around the inner wall; and a phase change material filing the sealed space.

9. The thermally conductive prosthetic socket of claim 8, wherein one or both of the inner wall and outer wall of the socket are comprised of a material selected from the group consisting of a resin doped with at least one conductive additive and an inherently thermally conductive resin formed by an additive manufacturing technique.

10. The thermally conductive prosthetic socket of claim 8, wherein the phase change material is a phase change gel material comprising a mixture of a phase change material, a thermal conductivity enhancing component, and a gelling component.

11. The thermally conductive prosthetic socket of claim 10, wherein the gelling component is a block copolymer.

12. The thermally conductive prosthetic socket of claim 10, wherein the thermal conductivity enhancing component is large aspect ratio graphene particles.

13. The thermally conductive prosthetic socket of claim 12, wherein the graphene particles are aligned.

14. The thermally conductive prosthetic socket of claim 8, wherein the phase change material is selected from the group consisting of octadecane and eicosane.

15. The thermally conductive prosthetic socket of claim 8, wherein the phase change material is a foam-type material resulting from air being mixed into the phase change material.

* * * * *